(12) United States Patent
Bustillo et al.

(10) Patent No.: US 9,841,398 B2
(45) Date of Patent: Dec. 12, 2017

(54) METHODS FOR MANUFACTURING WELL STRUCTURES FOR LOW-NOISE CHEMICAL SENSORS

(71) Applicant: LIFE TECHNOLOGIES CORPORATION, Carlsbad, CA (US)

(72) Inventors: James Bustillo, Castro Valley, CA (US); Shifeng Li, Fremont, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

(21) Appl. No.: 13/736,566

(22) Filed: Jan. 8, 2013

(65) Prior Publication Data

US 2014/0191293 A1   Jul. 10, 2014

(51) Int. Cl.
*H01L 29/66* (2006.01)
*G01N 27/414* (2006.01)

(52) U.S. Cl.
CPC ....... *G01N 27/414* (2013.01); *G01N 27/4148* (2013.01); *G01N 27/4145* (2013.01)

(58) Field of Classification Search
CPC .................................................. G01N 27/4148
USPC ....................................................... 257/243
See application file for complete search history.

(56) References Cited

U.S. PATENT DOCUMENTS

| | | | |
|---|---|---|---|
| 4,086,642 A | 4/1978 | Yoshida et al. | |
| 4,411,741 A | 10/1983 | Janata | |
| 4,438,354 A | 3/1984 | Haque et al. | |
| 4,444,644 A | 4/1984 | Hiramoto | |
| 4,490,678 A | 12/1984 | Kuisl et al. | |
| 4,641,084 A | 2/1987 | Komatsu | |
| 4,691,167 A | 9/1987 | Vlekkert et al. | |
| 4,701,253 A | 10/1987 | Ligtenberg et al. | |
| 4,722,830 A | 2/1988 | Urie et al. | |
| 4,743,954 A | 5/1988 | Brown | |
| 4,764,797 A | 8/1988 | Shaw et al. | |
| 4,777,019 A | 10/1988 | Dandekar | |
| 4,822,566 A | 4/1989 | Newman | |
| 4,863,849 A | 9/1989 | Melamede | |
| 4,864,229 A | 9/1989 | Lauks et al. | |
| 4,874,499 A | 10/1989 | Smith et al. | |

(Continued)

FOREIGN PATENT DOCUMENTS

| | | |
|---|---|---|
| CN | 1582334 | 2/2005 |
| CN | 1585896 | 2/2005 |

(Continued)

OTHER PUBLICATIONS

EP13174555.6 EP Extended Search Report Dec. 12, 2013.

(Continued)

*Primary Examiner* — Alexander Ghyka

(57) ABSTRACT

In one implementation, a method for manufacturing a chemical detection device is described. The method includes forming a chemical sensor having a sensing surface. A dielectric material is deposited on the sensing surface. A first etch process is performed to partially etch the dielectric material to define an opening over the sensing surface and leave remaining dielectric material on the sensing surface. An etch protect material is formed on a sidewall of the opening. A second etch process is then performed to selectively etch the remaining dielectric material using the etch protect material as an etch mask, thereby exposing the sensing surface.

6 Claims, 8 Drawing Sheets

(56) References Cited

U.S. PATENT DOCUMENTS

| | | |
|---|---|---|
| 4,893,088 A | 1/1990 | Myers et al. |
| 4,927,736 A | 5/1990 | Mueller et al. |
| 4,971,903 A | 11/1990 | Hyman |
| 5,009,766 A | 4/1991 | Lauks |
| 5,038,192 A | 8/1991 | Bonneau |
| 5,110,441 A | 5/1992 | Kinlen et al. |
| 5,113,870 A | 5/1992 | Rossenfeld |
| 5,126,759 A | 6/1992 | Small et al. |
| 5,138,251 A | 8/1992 | Koshiishi et al. |
| 5,140,393 A * | 8/1992 | Hijikihigawa et al. ....... 257/252 |
| 5,142,236 A | 8/1992 | Maloberti et al. |
| 5,151,587 A | 9/1992 | Machida et al. |
| 5,151,759 A | 9/1992 | Vinal |
| 5,164,319 A | 11/1992 | Hafeman et al. |
| 5,202,576 A | 4/1993 | Liu et al. |
| 5,284,566 A | 2/1994 | Cuomo et al. |
| 5,317,407 A | 5/1994 | Michon |
| 5,319,226 A | 6/1994 | Sohn et al. |
| 5,407,854 A | 4/1995 | Baxter et al. |
| 5,436,149 A | 7/1995 | Barnes |
| 5,439,839 A | 8/1995 | Jang |
| 5,466,348 A | 11/1995 | Holm-Kennedy |
| 5,475,337 A | 12/1995 | Tatsumi |
| 5,490,971 A | 2/1996 | Gifford et al. |
| 5,554,339 A | 9/1996 | Cozzette et al. |
| 5,583,462 A | 12/1996 | Grasshoff |
| 5,587,894 A | 12/1996 | Naruo |
| 5,593,838 A | 1/1997 | Zanzucchi et al. |
| 5,600,451 A | 2/1997 | Maki |
| 5,627,403 A | 5/1997 | Bacchetta et al. |
| 5,631,704 A | 5/1997 | Dickinson et al. |
| 5,637,469 A | 6/1997 | Wilding et al. |
| 5,646,558 A | 7/1997 | Jamshidi et al. |
| 5,702,964 A | 12/1997 | Lee |
| 5,793,230 A | 8/1998 | Chu et al. |
| 5,846,708 A | 12/1998 | Hollis et al. |
| 5,894,284 A | 4/1999 | Garrity et al. |
| 5,907,765 A | 5/1999 | Lescouzeres et al. |
| 5,911,873 A | 6/1999 | McCarron et al. |
| 5,912,560 A | 6/1999 | Pasternak |
| 5,922,591 A | 7/1999 | Anderson et al. |
| 5,923,421 A | 7/1999 | Rajic et al. |
| 5,944,970 A | 8/1999 | Rosenblatt |
| 5,958,703 A | 9/1999 | Dower et al. |
| 5,965,452 A | 10/1999 | Kovacs |
| 6,002,299 A | 12/1999 | Thomsen |
| 6,021,172 A | 2/2000 | Fossum et al. |
| 6,107,032 A | 8/2000 | Kilger et al. |
| 6,191,444 B1 | 2/2001 | Clampitt et al. |
| 6,195,585 B1 | 2/2001 | Karunasiri et al. |
| 6,210,891 B1 | 4/2001 | Nyren et al. |
| 6,255,678 B1 | 7/2001 | Sawada et al. |
| 6,262,568 B1 | 7/2001 | Komatsu et al. |
| 6,274,320 B1 | 8/2001 | Rothberg et al. |
| 6,275,061 B1 | 8/2001 | Tomita |
| 6,280,586 B1 | 8/2001 | Wolf et al. |
| 6,294,133 B1 | 9/2001 | Sawada et al. |
| 6,327,410 B1 | 12/2001 | Walt et al. |
| 6,353,324 B1 | 3/2002 | Uber, III et al. |
| 6,355,431 B1 | 3/2002 | Chee et al. |
| 6,361,671 B1 | 3/2002 | Mathies et al. |
| 6,372,291 B1 | 4/2002 | Hua et al. |
| 6,376,256 B1 | 4/2002 | Dunnington et al. |
| 6,384,684 B1 | 5/2002 | Redman-White |
| 6,403,957 B1 | 6/2002 | Fodor et al. |
| 6,406,848 B1 | 6/2002 | Bridgham et al. |
| 6,413,792 B1 | 7/2002 | Sauer et al. |
| 6,429,027 B1 | 8/2002 | Chee et al. |
| 6,432,360 B1 | 8/2002 | Church |
| 6,433,386 B1 | 8/2002 | Yun et al. |
| 6,459,398 B1 | 10/2002 | Gureshnik et al. |
| 6,465,178 B2 | 10/2002 | Chappa et al. |
| 6,475,728 B1 | 11/2002 | Martin et al. |
| 6,482,639 B2 | 11/2002 | Snow et al. |
| 6,485,944 B1 | 11/2002 | Church et al. |
| 6,490,220 B1 | 12/2002 | Merritt et al. |
| 6,499,499 B2 | 12/2002 | Dantsker et al. |
| 6,518,024 B2 | 2/2003 | Choong et al. |
| 6,518,146 B1 | 2/2003 | Singh et al. |
| 6,537,881 B1 | 3/2003 | Rangarajan et al. |
| 6,538,593 B2 | 3/2003 | Yang et al. |
| 6,545,620 B2 | 4/2003 | Groeneweg |
| 6,571,189 B2 | 5/2003 | Jensen et al. |
| 6,602,702 B1 | 8/2003 | McDevitt et al. |
| 6,605,428 B2 | 8/2003 | Klinger et al. |
| 6,613,513 B1 | 9/2003 | Parce et al. |
| 6,618,083 B1 | 9/2003 | Chen et al. |
| 6,624,637 B1 | 9/2003 | Pechstein |
| 6,627,154 B1 | 9/2003 | Goodman et al. |
| 6,654,505 B2 | 11/2003 | Bridgham et al. |
| 6,657,269 B2 | 12/2003 | Migliorato et al. |
| 6,671,341 B1 | 12/2003 | Kinget et al. |
| 6,682,899 B2 | 1/2004 | Bryan et al. |
| 6,682,936 B2 | 1/2004 | Kovacs |
| 6,686,638 B2 | 2/2004 | Fischer et al. |
| 6,700,814 B1 | 3/2004 | Nahas et al. |
| 6,703,660 B2 | 3/2004 | Yitzchaik et al. |
| 6,716,629 B2 | 4/2004 | Hess et al. |
| 6,762,022 B2 | 7/2004 | Makarov et al. |
| 6,770,472 B2 | 8/2004 | Manalis et al. |
| 6,780,591 B2 | 8/2004 | Williams et al. |
| 6,795,006 B1 | 9/2004 | Delight et al. |
| 6,806,052 B2 | 10/2004 | Bridgham et al. |
| 6,828,100 B1 | 12/2004 | Ronaghi |
| 6,831,994 B2 | 12/2004 | Bridgham et al. |
| 6,841,128 B2 | 1/2005 | Kambara et al. |
| 6,859,570 B2 | 2/2005 | Walt et al. |
| 6,878,255 B1 | 4/2005 | Wang et al. |
| 6,888,194 B2 | 5/2005 | Yoshino |
| 6,898,121 B2 | 5/2005 | Chien et al. |
| 6,906,524 B2 | 6/2005 | Chung et al. |
| 6,919,211 B1 | 7/2005 | Fodor et al. |
| 6,926,865 B2 | 8/2005 | Howard |
| 6,927,045 B2 | 8/2005 | Hadd et al. |
| 6,929,944 B2 | 8/2005 | Matson |
| 6,939,451 B2 | 9/2005 | Zhao et al. |
| 6,953,958 B2 | 10/2005 | Baxter et al. |
| 6,958,216 B2 | 10/2005 | Kelley et al. |
| 6,969,488 B2 | 11/2005 | Bridgham et al. |
| 6,998,274 B2 | 2/2006 | Chee et al. |
| 7,008,550 B2 | 3/2006 | Li et al. |
| 7,019,305 B2 | 3/2006 | Eversmann et al. |
| 7,022,288 B1 | 4/2006 | Boss |
| 7,033,754 B2 | 4/2006 | Chee et al. |
| 7,037,687 B2 | 5/2006 | Williams et al. |
| 7,045,097 B2 | 5/2006 | Kovacs |
| 7,049,645 B2 | 5/2006 | Sawada et al. |
| 7,060,431 B2 | 6/2006 | Chee et al. |
| 7,067,886 B2 | 6/2006 | Bonges et al. |
| 7,084,641 B2 | 8/2006 | Brederlow et al. |
| 7,085,502 B2 | 8/2006 | Shushakob et al. |
| 7,087,387 B2 | 8/2006 | Gerdes et al. |
| 7,090,975 B2 | 8/2006 | Shultz et al. |
| 7,091,059 B2 | 8/2006 | Rhodes |
| 7,092,757 B2 | 8/2006 | Larson et al. |
| 7,097,973 B1 | 8/2006 | Zenhausern |
| 7,105,300 B2 | 9/2006 | Parce et al. |
| 7,106,089 B2 | 9/2006 | Nakano et al. |
| 7,129,554 B2 | 10/2006 | Lieber et al. |
| 7,169,560 B2 | 1/2007 | Lapidus et al. |
| 7,173,445 B2 | 2/2007 | Fujii et al. |
| 7,190,026 B2 | 3/2007 | Lotfi et al. |
| 7,192,745 B2 | 3/2007 | Jaeger |
| 7,193,453 B2 | 3/2007 | Wei et al. |
| 7,211,390 B2 | 5/2007 | Rothberg et al. |
| 7,220,550 B2 | 5/2007 | Keen |
| 7,223,540 B2 | 5/2007 | Pourmand et al. |
| 7,226,734 B2 | 6/2007 | Chee et al. |
| 7,229,799 B2 | 6/2007 | Williams et al. |
| 7,235,389 B2 | 6/2007 | Lim et al. |
| 7,238,323 B2 | 7/2007 | Knapp et al. |
| 7,239,188 B1 | 7/2007 | Xu et al. |
| 7,244,559 B2 | 7/2007 | Rothberg et al. |
| 7,244,567 B2 | 7/2007 | Chen et al. |

(56) References Cited

U.S. PATENT DOCUMENTS

| | | |
|---|---|---|
| 7,264,929 B2 | 9/2007 | Rothberg et al. |
| 7,264,934 B2 | 9/2007 | Fuller |
| 7,265,929 B2 | 9/2007 | Umeda et al. |
| 7,267,751 B2 | 9/2007 | Gelbart et al. |
| 7,276,749 B2 | 10/2007 | Martin et al. |
| 7,279,588 B2 | 10/2007 | Hong et al. |
| 7,282,370 B2 | 10/2007 | Bridgham et al. |
| 7,285,384 B2 | 10/2007 | Fan et al. |
| 7,291,496 B2 | 11/2007 | Holm-Kennedy |
| 7,297,518 B2 | 11/2007 | Quake et al. |
| 7,298,475 B2 | 11/2007 | Gandhi et al. |
| 7,303,875 B1 | 12/2007 | Bock et al. |
| 7,317,216 B2 | 1/2008 | Holm-Kennedy |
| 7,317,484 B2 | 1/2008 | Dosluoglu et al. |
| 7,323,305 B2 | 1/2008 | Leamon et al. |
| 7,335,526 B2 | 2/2008 | Peters et al. |
| 7,335,762 B2 | 2/2008 | Rothberg et al. |
| 7,361,946 B2 | 4/2008 | Johnson et al. |
| 7,363,717 B2 | 4/2008 | Ekseth et al. |
| 7,381,936 B2 | 6/2008 | Tan et al. |
| 7,394,263 B2 | 7/2008 | Pechstein et al. |
| 7,419,636 B2 | 9/2008 | Aker et al. |
| 7,425,431 B2 | 9/2008 | Church et al. |
| 7,455,971 B2 | 11/2008 | Chee et al. |
| 7,462,452 B2 | 12/2008 | Williams et al. |
| 7,462,512 B2 | 12/2008 | Levon et al. |
| 7,462,709 B2 | 12/2008 | Jaeger |
| 7,465,512 B2 | 12/2008 | Wright et al. |
| 7,466,258 B1 | 12/2008 | Akopyan et al. |
| 7,470,352 B2 | 12/2008 | Eversmann et al. |
| 7,476,504 B2 | 1/2009 | Turner |
| 7,482,153 B2 | 1/2009 | Okada et al. |
| 7,482,677 B2 | 1/2009 | Lee et al. |
| 7,499,513 B1 | 3/2009 | Tetzlaff et al. |
| 7,515,124 B2 | 4/2009 | Yaguma et al. |
| 7,534,097 B2 | 5/2009 | Wong et al. |
| 7,538,827 B2 | 5/2009 | Chou |
| 7,575,865 B2 | 8/2009 | Leamon et al. |
| 7,576,037 B2 | 8/2009 | Engelhardt et al. |
| 7,595,883 B1 | 9/2009 | El Gamal et al. |
| 7,605,650 B2 | 10/2009 | Forbes |
| 7,608,810 B2 | 10/2009 | Yamada |
| 7,609,093 B2 | 10/2009 | Sarig et al. |
| 7,609,303 B1 | 10/2009 | Lee |
| 7,612,369 B2 | 11/2009 | Stasiak |
| 7,612,817 B2 | 11/2009 | Tay |
| 7,614,135 B2 | 11/2009 | Santini, Jr. et al. |
| 7,622,294 B2 | 11/2009 | Walt et al. |
| 7,645,596 B2 | 1/2010 | Williams et al. |
| 7,649,358 B2 | 1/2010 | Toumazou et al. |
| 7,667,501 B2 | 2/2010 | Surendranath et al. |
| 7,686,929 B2 | 3/2010 | Toumazou et al. |
| 7,695,907 B2 | 4/2010 | Miyahara et al. |
| 7,733,401 B2 | 6/2010 | Takeda |
| 7,772,383 B2 | 8/2010 | Chakrabarti et al. |
| 7,785,785 B2 | 8/2010 | Pourmand et al. |
| 7,785,790 B1 | 8/2010 | Church et al. |
| 7,794,584 B2 | 9/2010 | Chodavarapu et al. |
| 7,821,806 B2 | 10/2010 | Horiuchi |
| 7,824,900 B2 | 11/2010 | Iwadate et al. |
| 7,838,226 B2 | 11/2010 | Kamahori et al. |
| 7,842,377 B2 | 11/2010 | Lanphere et al. |
| 7,842,457 B2 | 11/2010 | Berka et al. |
| 7,859,029 B2 | 12/2010 | Lee et al. |
| 7,859,291 B2 | 12/2010 | Kim |
| 7,875,440 B2 | 1/2011 | Williams et al. |
| 7,884,398 B2 | 2/2011 | Levon et al. |
| 7,885,490 B2 | 2/2011 | Heideman et al. |
| 7,888,013 B2 | 2/2011 | Miyahara et al. |
| 7,888,015 B2 | 2/2011 | Toumazou et al. |
| 7,888,708 B2 | 2/2011 | Yazawa et al. |
| 7,890,891 B2 | 2/2011 | Stuber et al. |
| 7,898,277 B2 | 3/2011 | Weir |
| 7,923,240 B2 | 4/2011 | Su |
| 7,927,797 B2 | 4/2011 | Nobile et al. |
| 7,932,034 B2 | 4/2011 | Esfandyarpour et al. |
| 7,948,015 B2 | 5/2011 | Rothberg et al. |
| 7,955,995 B2 | 6/2011 | Kakehata et al. |
| 7,960,776 B2 | 6/2011 | Kim et al. |
| 7,972,828 B2 | 7/2011 | Ward et al. |
| 7,981,362 B2 | 7/2011 | Glezer et al. |
| 8,012,690 B2 | 9/2011 | Berka et al. |
| 8,017,938 B2 | 9/2011 | Gomez et al. |
| 8,035,175 B2 | 10/2011 | Shim et al. |
| 8,052,863 B2 | 11/2011 | Suzuki et al. |
| 8,067,731 B2 | 11/2011 | Matyjaszczyk et al. |
| 8,072,188 B2 | 12/2011 | Yorinobu et al. |
| 8,114,591 B2 | 2/2012 | Toumazou et al. |
| 8,124,936 B1 | 2/2012 | Lagna |
| 8,133,698 B2 | 3/2012 | Silver |
| 8,138,496 B2 | 3/2012 | Li et al. |
| 8,154,480 B2 | 4/2012 | Shishido et al. |
| 8,199,859 B2 | 6/2012 | Zerbe et al. |
| 8,217,433 B1 | 7/2012 | Fife |
| 8,227,877 B2 | 7/2012 | Lee et al. |
| 8,231,831 B2 | 7/2012 | Hartzell et al. |
| 8,232,582 B2 | 7/2012 | Sauer et al. |
| 8,232,813 B2 | 7/2012 | Burdett et al. |
| 8,247,849 B2 | 8/2012 | Fife et al. |
| 8,248,356 B2 | 8/2012 | Chen |
| 8,262,900 B2 | 9/2012 | Rothberg et al. |
| 8,263,336 B2 | 9/2012 | Rothberg et al. |
| 8,264,014 B2 | 9/2012 | Rothberg et al. |
| 8,269,261 B2 | 9/2012 | Rothberg et al. |
| 8,277,628 B2 | 10/2012 | Ronaghi et al. |
| 8,293,082 B2 | 10/2012 | Rothberg et al. |
| 8,306,757 B2 | 11/2012 | Rothberg et al. |
| 8,313,625 B2 | 11/2012 | Rothberg et al. |
| 8,313,639 B2 | 11/2012 | Rothberg et al. |
| 8,317,999 B2 | 11/2012 | Rothberg et al. |
| 8,340,914 B2 | 12/2012 | Gatewood et al. |
| 8,343,856 B2 | 1/2013 | Therrien et al. |
| 8,349,167 B2 | 1/2013 | Rothberg et al. |
| 8,357,547 B2 | 1/2013 | Lee et al. |
| 8,361,713 B2 | 1/2013 | Bridgham et al. |
| 8,383,396 B2 | 2/2013 | Kamahori et al. |
| 8,415,716 B2 | 4/2013 | Rothberg et al. |
| 8,421,437 B2 | 4/2013 | Levine |
| 8,426,898 B2 | 4/2013 | Rothberg et al. |
| 8,426,899 B2 | 4/2013 | Rothberg et al. |
| 8,435,395 B2 | 5/2013 | Rothberg et al. |
| 8,441,044 B2 | 5/2013 | Rothberg et al. |
| 8,445,194 B2 | 5/2013 | Drmanac et al. |
| 8,445,945 B2 | 5/2013 | Rothberg et al. |
| 8,450,781 B2 | 5/2013 | Rothberg et al. |
| 8,470,164 B2 | 6/2013 | Rothberg et al. |
| 8,487,790 B2 | 7/2013 | Fife et al. |
| 8,492,800 B2 | 7/2013 | Rothberg et al. |
| 8,496,802 B2 | 7/2013 | Rothberg et al. |
| 8,502,278 B2 | 8/2013 | Rothberg et al. |
| 8,519,448 B2 | 8/2013 | Rothberg et al. |
| 8,524,057 B2 | 9/2013 | Rothberg et al. |
| 8,530,941 B2 | 9/2013 | Rothberg et al. |
| 8,535,513 B2 | 9/2013 | Rothberg et al. |
| 8,552,771 B1 | 10/2013 | Jordan et al. |
| 8,558,288 B2 | 10/2013 | Rothberg et al. |
| 8,575,664 B2 | 11/2013 | Rothberg et al. |
| 8,592,154 B2 | 11/2013 | Rearick et al. |
| 8,653,567 B2 | 2/2014 | Fife |
| 8,658,017 B2 | 2/2014 | Rothberg et al. |
| 8,673,627 B2 | 3/2014 | Nobile et al. |
| 8,685,230 B2 | 4/2014 | Rothberg et al. |
| 8,685,298 B2 | 4/2014 | Rothberg et al. |
| 8,728,844 B1 | 5/2014 | Liu et al. |
| 8,731,847 B2 | 5/2014 | Johnson et al. |
| 8,742,469 B2 | 6/2014 | Milgrew |
| 8,742,472 B2 | 6/2014 | Rothberg et al. |
| 8,747,748 B2 | 6/2014 | Li et al. |
| 8,764,969 B2 | 7/2014 | Rothberg et al. |
| 8,766,327 B2 | 7/2014 | Milgrew |
| 8,766,328 B2 | 7/2014 | Rothberg et al. |
| 8,786,331 B2 | 7/2014 | Jordan et al. |
| 8,796,036 B2 | 8/2014 | Fife et al. |
| 8,821,798 B2 | 9/2014 | Bustillo et al. |

(56) References Cited

U.S. PATENT DOCUMENTS

| | | |
|---|---|---|
| 8,841,217 B1 | 9/2014 | Fife et al. |
| 8,847,637 B1 | 9/2014 | Guyton |
| 8,912,005 B1 | 12/2014 | Fife et al. |
| 8,945,912 B2 | 2/2015 | Bashir et al. |
| 8,962,366 B2 | 2/2015 | Putnam et al. |
| 8,963,216 B2 | 2/2015 | Fife et al. |
| 8,983,783 B2 | 3/2015 | Johnson et al. |
| 9,023,674 B2 | 5/2015 | Shen et al. |
| 9,164,070 B2 | 10/2015 | Fife |
| 9,201,041 B2 | 12/2015 | Dalton et al. |
| 9,270,264 B2 | 2/2016 | Jordan et al. |
| 9,389,199 B2 | 7/2016 | Cheng et al. |
| 2001/0007418 A1 | 7/2001 | Komatsu et al. |
| 2001/0024790 A1 | 9/2001 | Kambara et al. |
| 2002/0001801 A1 | 1/2002 | Fan et al. |
| 2002/0012930 A1 | 1/2002 | Rothberg et al. |
| 2002/0012933 A1 | 1/2002 | Rothberg et al. |
| 2002/0012937 A1 | 1/2002 | Tender et al. |
| 2002/0029971 A1 | 3/2002 | Kovacs |
| 2002/0042059 A1 | 4/2002 | Makarov et al. |
| 2002/0042388 A1 | 4/2002 | Cooper et al. |
| 2002/0050611 A1 | 5/2002 | Yitzchaik et al. |
| 2002/0061529 A1 | 5/2002 | Bridgham et al. |
| 2002/0081714 A1 | 6/2002 | Jain et al. |
| 2002/0085136 A1 | 7/2002 | Moon et al. |
| 2002/0086318 A1 | 7/2002 | Manalis et al. |
| 2002/0094533 A1 | 7/2002 | Hess et al. |
| 2002/0117694 A1 | 8/2002 | Migliorato et al. |
| 2002/0150909 A1 | 10/2002 | Stuelpnagel et al. |
| 2002/0168678 A1 | 11/2002 | Williams et al. |
| 2003/0020334 A1 | 1/2003 | Nozu et al. |
| 2003/0032052 A1 | 2/2003 | Hadd et al. |
| 2003/0044799 A1 | 3/2003 | Matson |
| 2003/0044833 A1 | 3/2003 | Benchikh et al. |
| 2003/0054396 A1 | 3/2003 | Weiner |
| 2003/0064366 A1 | 4/2003 | Hardin et al. |
| 2003/0068629 A1 | 4/2003 | Rothberg et al. |
| 2003/0100102 A1 | 5/2003 | Rothberg et al. |
| 2003/0102510 A1 | 6/2003 | Lim et al. |
| 2003/0108867 A1 | 6/2003 | Chee et al. |
| 2003/0119020 A1 | 6/2003 | Stevens et al. |
| 2003/0124572 A1 | 7/2003 | Umek et al. |
| 2003/0124599 A1 | 7/2003 | Chen et al. |
| 2003/0141928 A1 | 7/2003 | Lee |
| 2003/0148301 A1 | 8/2003 | Aono et al. |
| 2003/0148344 A1 | 8/2003 | Rothberg et al. |
| 2003/0152994 A1 | 8/2003 | Woudenberg et al. |
| 2003/0155942 A1 | 8/2003 | Thewes et al. |
| 2003/0175990 A1 | 9/2003 | Hayenga et al. |
| 2003/0186262 A1 | 10/2003 | Cailloux |
| 2003/0211502 A1 | 11/2003 | Sauers et al. |
| 2003/0215791 A1 | 11/2003 | Garini et al. |
| 2003/0215857 A1 | 11/2003 | Kilger et al. |
| 2003/0224419 A1 | 12/2003 | Corcoran et al. |
| 2003/0231531 A1 | 12/2003 | Baxter et al. |
| 2004/0002470 A1 | 1/2004 | Keith et al. |
| 2004/0023253 A1 | 2/2004 | Kunwar et al. |
| 2004/0038420 A1 | 2/2004 | Gelbart et al. |
| 2004/0079636 A1 | 4/2004 | Hsia et al. |
| 2004/0106211 A1 | 6/2004 | Kauer et al. |
| 2004/0121354 A1 | 6/2004 | Yazawa et al. |
| 2004/0130377 A1 | 7/2004 | Takeda et al. |
| 2004/0136866 A1 | 7/2004 | Pontis et al. |
| 2004/0146849 A1 | 7/2004 | Huang et al. |
| 2004/0185484 A1 | 9/2004 | Costa et al. |
| 2004/0185591 A1 | 9/2004 | Hsiung et al. |
| 2004/0197803 A1 | 10/2004 | Yaku et al. |
| 2004/0235216 A1 | 11/2004 | Rhodes |
| 2004/0248161 A1 | 12/2004 | Rothberg et al. |
| 2005/0006234 A1 | 1/2005 | Hassibi |
| 2005/0009022 A1 | 1/2005 | Weiner et al. |
| 2005/0017190 A1 | 1/2005 | Eversmann et al. |
| 2005/0031490 A1 | 2/2005 | Gumbrecht et al. |
| 2005/0032075 A1 | 2/2005 | Yaku et al. |
| 2005/0032076 A1 | 2/2005 | Williams et al. |
| 2005/0058990 A1 | 3/2005 | Guia et al. |
| 2005/0062093 A1 | 3/2005 | Sawada et al. |
| 2005/0079510 A1 | 4/2005 | Berka et al. |
| 2005/0093072 A1 | 5/2005 | Bonges et al. |
| 2005/0093645 A1 | 5/2005 | Watanabe et al. |
| 2005/0106587 A1 | 5/2005 | Klapproth |
| 2005/0142033 A1 | 6/2005 | Glezer et al. |
| 2005/0151181 A1 | 7/2005 | Beintner et al. |
| 2005/0156207 A1 | 7/2005 | Yazawa et al. |
| 2005/0156584 A1 | 7/2005 | Feng |
| 2005/0181440 A1 | 8/2005 | Chee et al. |
| 2005/0189960 A1 | 9/2005 | Tajima |
| 2005/0191698 A1 | 9/2005 | Chee et al. |
| 2005/0202582 A1 | 9/2005 | Eversmann et al. |
| 2005/0206548 A1 | 9/2005 | Muramatsu et al. |
| 2005/0212016 A1 | 9/2005 | Brunner et al. |
| 2005/0221473 A1 | 10/2005 | Dubin et al. |
| 2005/0230245 A1 | 10/2005 | Morgenshtein et al. |
| 2005/0230271 A1 | 10/2005 | Levon et al. |
| 2005/0233318 A1 | 10/2005 | Chee et al. |
| 2005/0239132 A1 | 10/2005 | Klapprith |
| 2005/0266456 A1 | 12/2005 | Williams et al. |
| 2005/0282224 A1 | 12/2005 | Fouillet et al. |
| 2005/0285155 A1 | 12/2005 | Johnson et al. |
| 2006/0000772 A1 | 1/2006 | Sano et al. |
| 2006/0024711 A1 | 2/2006 | Lapidus et al. |
| 2006/0035400 A1 | 2/2006 | Wu et al. |
| 2006/0040297 A1 | 2/2006 | Leamon et al. |
| 2006/0057025 A1 | 3/2006 | Eversmann et al. |
| 2006/0057604 A1 | 3/2006 | Chen et al. |
| 2006/0073513 A1 | 4/2006 | Chee et al. |
| 2006/0141474 A1 | 6/2006 | Miyahara et al. |
| 2006/0154399 A1 | 7/2006 | Sauer et al. |
| 2006/0166203 A1 | 7/2006 | Tooke et al. |
| 2006/0182664 A1 | 8/2006 | Peck et al. |
| 2006/0197118 A1 | 9/2006 | Migliorato et al. |
| 2006/0199193 A1 | 9/2006 | Koo et al. |
| 2006/0199493 A1 | 9/2006 | Hartmann et al. |
| 2006/0205061 A1 | 9/2006 | Roukes |
| 2006/0216812 A1 | 9/2006 | Okada et al. |
| 2006/0219558 A1 | 10/2006 | Hafeman et al. |
| 2006/0228721 A1 | 10/2006 | Leamon et al. |
| 2006/0246497 A1 | 11/2006 | Huang et al. |
| 2006/0269927 A1 | 11/2006 | Lieber |
| 2006/0289726 A1 | 12/2006 | Paulus et al. |
| 2007/0059741 A1 | 3/2007 | Kamahori et al. |
| 2007/0069291 A1 | 3/2007 | Stuber et al. |
| 2007/0087401 A1 | 4/2007 | Neilson et al. |
| 2007/0092872 A1 | 4/2007 | Rothberg et al. |
| 2007/0095663 A1 | 5/2007 | Chou et al. |
| 2007/0096164 A1 | 5/2007 | Peters et al. |
| 2007/0099173 A1 | 5/2007 | Spira et al. |
| 2007/0099208 A1 | 5/2007 | Drmanac et al. |
| 2007/0117099 A1 | 5/2007 | Engelhardt et al. |
| 2007/0138132 A1 | 6/2007 | Barth |
| 2007/0172865 A1 | 7/2007 | Hardin et al. |
| 2007/0212681 A1 | 9/2007 | Shapiro et al. |
| 2007/0217963 A1 | 9/2007 | Elizarov et al. |
| 2007/0231824 A1 | 10/2007 | Chee et al. |
| 2007/0233477 A1 | 10/2007 | Halowani et al. |
| 2007/0247170 A1 | 10/2007 | Barbaro et al. |
| 2007/0250274 A1 | 10/2007 | Volkov et al. |
| 2007/0252176 A1 | 11/2007 | Shim et al. |
| 2007/0262363 A1 | 11/2007 | Tao et al. |
| 2007/0278488 A1 | 12/2007 | Hirabayashi et al. |
| 2008/0003142 A1 | 1/2008 | Link et al. |
| 2008/0012007 A1 | 1/2008 | Li et al. |
| 2008/0014589 A1 | 1/2008 | Link et al. |
| 2008/0035494 A1 | 2/2008 | Gomez et al. |
| 2008/0047836 A1 | 2/2008 | Strand et al. |
| 2008/0063566 A1 | 3/2008 | Matsumoto et al. |
| 2008/0085219 A1 | 4/2008 | Beebe et al. |
| 2008/0094074 A1 | 4/2008 | Kim et al. |
| 2008/0096216 A1 | 4/2008 | Quake et al. |
| 2008/0111161 A1 | 5/2008 | Sorge et al. |
| 2008/0115361 A1 | 5/2008 | Santini et al. |
| 2008/0121946 A1 | 5/2008 | Youn et al. |
| 2008/0132693 A1 | 6/2008 | Berka et al. |
| 2008/0136933 A1 | 6/2008 | Dosluoglu et al. |

(56) References Cited

U.S. PATENT DOCUMENTS

| | | |
|---|---|---|
| 2008/0164917 A1 | 7/2008 | Floyd et al. |
| 2008/0176271 A1 | 7/2008 | Silver et al. |
| 2008/0185616 A1 | 8/2008 | Johnson et al. |
| 2008/0197022 A1 | 8/2008 | Suzuki et al. |
| 2008/0204048 A1 | 8/2008 | Stasiak et al. |
| 2008/0205559 A1 | 8/2008 | Iida |
| 2008/0210931 A1 | 9/2008 | Truong et al. |
| 2008/0230386 A1 | 9/2008 | Srinivasan et al. |
| 2009/0026082 A1 | 1/2009 | Rothberg et al. |
| 2009/0030117 A1 | 1/2009 | Lanphere et al. |
| 2009/0033370 A1 | 2/2009 | Sarig et al. |
| 2009/0048124 A1 | 2/2009 | Leamon et al. |
| 2009/0062132 A1 | 3/2009 | Bortner |
| 2009/0075838 A1 | 3/2009 | El Gamal et al. |
| 2009/0079414 A1 | 3/2009 | Levon et al. |
| 2009/0120905 A1 | 5/2009 | Kohl et al. |
| 2009/0121258 A1 | 5/2009 | Kumar |
| 2009/0127589 A1 | 5/2009 | Rothberg |
| 2009/0127689 A1 | 5/2009 | Ye et al. |
| 2009/0140763 A1 | 6/2009 | Kim |
| 2009/0149607 A1 | 6/2009 | Karim et al. |
| 2009/0156425 A1 | 6/2009 | Walt et al. |
| 2009/0170728 A1 | 7/2009 | Walt et al. |
| 2009/0194416 A1 | 8/2009 | Hsiung et al. |
| 2009/0201032 A1 | 8/2009 | Burdett et al. |
| 2009/0273386 A1 | 11/2009 | Korobeynikov et al. |
| 2010/0007326 A1 | 1/2010 | Nakazato |
| 2010/0026814 A1 | 2/2010 | Shimoda |
| 2010/0039146 A1 | 2/2010 | Park et al. |
| 2010/0052765 A1 | 3/2010 | Makino |
| 2010/0105373 A1 | 4/2010 | Kanade |
| 2010/0133547 A1 | 6/2010 | Kunze et al. |
| 2010/0137143 A1 | 6/2010 | Rothberg et al. |
| 2010/0156454 A1 | 6/2010 | Weir |
| 2010/0176463 A1 | 7/2010 | Koizumi et al. |
| 2010/0188073 A1 | 7/2010 | Rothberg et al. |
| 2010/0197507 A1 | 8/2010 | Rothberg et al. |
| 2010/0244106 A1 | 9/2010 | Parker et al. |
| 2010/0273166 A1 | 10/2010 | Garcia |
| 2010/0282617 A1 | 11/2010 | Rothberg et al. |
| 2010/0300895 A1 | 12/2010 | Nobile et al. |
| 2010/0301398 A1 | 12/2010 | Rothberg et al. |
| 2011/0037121 A1 | 2/2011 | Lee et al. |
| 2011/0062972 A1 | 3/2011 | Je et al. |
| 2011/0114827 A1 | 5/2011 | Yamaoka et al. |
| 2011/0165557 A1 | 7/2011 | Ah et al. |
| 2011/0169056 A1 | 7/2011 | Wey et al. |
| 2011/0181253 A1 | 7/2011 | Isham et al. |
| 2011/0217697 A1 | 9/2011 | Rothberg et al. |
| 2011/0230375 A1 | 9/2011 | Rothberg et al. |
| 2011/0236263 A1 | 9/2011 | Sawada et al. |
| 2011/0247933 A1 | 10/2011 | Rothberg et al. |
| 2011/0248320 A1 | 10/2011 | Rothberg et al. |
| 2011/0262903 A1 | 10/2011 | Davidson et al. |
| 2011/0263463 A1 | 10/2011 | Rothberg et al. |
| 2011/0275522 A1 | 11/2011 | Rothberg et al. |
| 2011/0281737 A1 | 11/2011 | Rothberg et al. |
| 2011/0281741 A1 | 11/2011 | Rothberg et al. |
| 2011/0287945 A1 | 11/2011 | Rothberg et al. |
| 2011/0299337 A1 | 12/2011 | Parris et al. |
| 2012/0000274 A1 | 1/2012 | Fife |
| 2012/0001056 A1 | 1/2012 | Fife et al. |
| 2012/0001235 A1 | 1/2012 | Fife |
| 2012/0001236 A1 | 1/2012 | Fife et al. |
| 2012/0001237 A1 | 1/2012 | Fife et al. |
| 2012/0001646 A1 | 1/2012 | Bolander et al. |
| 2012/0012900 A1 | 1/2012 | Lee et al. |
| 2012/0013392 A1 | 1/2012 | Rothberg et al. |
| 2012/0022795 A1 | 1/2012 | Johnson et al. |
| 2012/0034607 A1 | 2/2012 | Rothberg et al. |
| 2012/0037961 A1 | 2/2012 | Rothberg et al. |
| 2012/0045368 A1 | 2/2012 | Hinz et al. |
| 2012/0045844 A1 | 2/2012 | Rothberg et al. |
| 2012/0055811 A1 | 3/2012 | Rothberg et al. |
| 2012/0055813 A1 | 3/2012 | Rothberg et al. |
| 2012/0056248 A1 | 3/2012 | Fife et al. |
| 2012/0060587 A1 | 3/2012 | Babcock et al. |
| 2012/0074956 A1 | 3/2012 | Fife et al. |
| 2012/0129703 A1 | 5/2012 | Rothberg et al. |
| 2012/0129728 A1 | 5/2012 | Rothberg et al. |
| 2012/0129732 A1 | 5/2012 | Rothberg et al. |
| 2012/0135870 A1 | 5/2012 | Rothberg et al. |
| 2012/0143531 A1 | 6/2012 | Davey et al. |
| 2012/0154018 A1 | 6/2012 | Sugiura |
| 2012/0161207 A1 | 6/2012 | Homyk et al. |
| 2012/0173159 A1 | 7/2012 | Davey et al. |
| 2012/0228136 A1 | 9/2012 | Levine |
| 2012/0247977 A1 | 10/2012 | Rothberg et al. |
| 2012/0249192 A1 | 10/2012 | Matsushita |
| 2012/0261274 A1 | 10/2012 | Rearick et al. |
| 2012/0265474 A1 | 10/2012 | Rearick et al. |
| 2012/0279859 A1 | 11/2012 | Rothberg et al. |
| 2012/0280285 A1 | 11/2012 | Rothberg et al. |
| 2012/0280286 A1 | 11/2012 | Rothberg et al. |
| 2012/0283146 A1 | 11/2012 | Rothberg et al. |
| 2012/0286332 A1 | 11/2012 | Rothberg et al. |
| 2012/0286333 A1 | 11/2012 | Rothberg et al. |
| 2012/0286771 A1 | 11/2012 | Rothberg et al. |
| 2012/0288853 A1 | 11/2012 | Rothberg et al. |
| 2012/0288976 A1 | 11/2012 | Rothberg et al. |
| 2012/0289413 A1 | 11/2012 | Rothberg et al. |
| 2012/0293158 A1 | 11/2012 | Rothberg et al. |
| 2012/0295795 A1 | 11/2012 | Rothberg et al. |
| 2012/0322054 A1 | 12/2012 | Rothberg et al. |
| 2012/0325683 A1 | 12/2012 | Milgrew |
| 2012/0326213 A1 | 12/2012 | Bustillo et al. |
| 2012/0326767 A1 | 12/2012 | Milgrew |
| 2012/0329043 A1 | 12/2012 | Milgrew |
| 2012/0329044 A1 | 12/2012 | Milgrew |
| 2012/0329192 A1 | 12/2012 | Bustillo et al. |
| 2013/0001653 A1 | 1/2013 | Milgrew |
| 2013/0004948 A1 | 1/2013 | Milgrew |
| 2013/0004949 A1 | 1/2013 | Rearick et al. |
| 2013/0009214 A1 | 1/2013 | Bustillo et al. |
| 2013/0015505 A1 | 1/2013 | Rothberg et al. |
| 2013/0015506 A1 | 1/2013 | Rothberg et al. |
| 2013/0017959 A1 | 1/2013 | Rothberg et al. |
| 2013/0056353 A1 | 3/2013 | Nemirovsky et al. |
| 2013/0105868 A1 | 5/2013 | Kalnitsky et al. |
| 2013/0135018 A1 | 5/2013 | Kuo et al. |
| 2013/0210128 A1 | 8/2013 | Rothberg et al. |
| 2013/0210182 A1 | 8/2013 | Rothberg et al. |
| 2013/0210641 A1 | 8/2013 | Rothberg et al. |
| 2013/0217004 A1 | 8/2013 | Rothberg et al. |
| 2013/0217587 A1 | 8/2013 | Rothberg et al. |
| 2013/0281307 A1 | 10/2013 | Li et al. |
| 2013/0324421 A1 | 12/2013 | Rothberg et al. |
| 2013/0341734 A1 | 12/2013 | Merz |
| 2014/0080717 A1 | 3/2014 | Li et al. |
| 2014/0148345 A1 | 5/2014 | Li et al. |
| 2014/0234981 A1 | 8/2014 | Zarkesh-Ha et al. |
| 2014/0235452 A1 | 8/2014 | Rothberg et al. |
| 2014/0235463 A1 | 8/2014 | Rothberg et al. |
| 2014/0308752 A1 | 10/2014 | Chang et al. |
| 2015/0097214 A1 | 4/2015 | Chen et al. |
| 2016/0178568 A1 | 6/2016 | Cheng et al. |

FOREIGN PATENT DOCUMENTS

| | | |
|---|---|---|
| CN | 1703623 | 11/2005 |
| CN | 1826525 | 8/2006 |
| CN | 101669026 | 3/2010 |
| CN | 101676714 | 3/2010 |
| CN | 102203282 | 9/2011 |
| CN | 102301228 | 12/2011 |
| CN | 102484267 | 5/2012 |
| DE | 4232532 | 4/1994 |
| DE | 4430811 | 9/1995 |
| DE | 102004044299 | 3/2006 |
| DE | 102008012899 | 9/2009 |
| EP | 0223618 | 5/1987 |
| EP | 1243925 A2 | 9/2002 |
| EP | 1243925 A3 | 3/2003 |
| EP | 1371974 | 12/2003 |

(56) References Cited

FOREIGN PATENT DOCUMENTS

| | | |
|---|---|---|
| EP | 1432818 | 6/2004 |
| EP | 1542009 | 6/2005 |
| EP | 1557884 | 7/2005 |
| EP | 1669749 | 6/2006 |
| EP | 1870703 | 12/2007 |
| EP | 2307577 | 4/2011 |
| GB | 2457851 | 9/2009 |
| GB | 2461127 | 12/2009 |
| GB | 2461127 B | 7/2010 |
| JP | 58070155 | 4/1983 |
| JP | 62-237349 | 10/1987 |
| JP | 02-250331 | 10/1990 |
| JP | 02-310931 | 12/1990 |
| JP | H05-080115 | 4/1993 |
| JP | 2002-221510 | 8/2002 |
| JP | 2002/272463 | 9/2002 |
| JP | 2002272463 | 9/2002 |
| JP | PCT/JP2003/04697 | 4/2003 |
| JP | 2003-279532 | 10/2003 |
| JP | 2003-322633 | 11/2003 |
| JP | 2004-510125 | 4/2004 |
| JP | 2005218310 | 8/2004 |
| JP | 2004-271384 | 9/2004 |
| JP | 05077210 | 3/2005 |
| JP | 2005077210 | 3/2005 |
| JP | 2005-515475 | 5/2005 |
| JP | 2005518541 | 6/2005 |
| JP | 2005-207797 | 8/2005 |
| JP | 06138846 | 6/2006 |
| JP | 2006-284225 | 10/2006 |
| JP | 2007/243003 | 9/2007 |
| JP | 2008-215974 | 9/2008 |
| JP | 2010513869 | 4/2010 |
| JP | 2011525810 | 9/2011 |
| JP | 2012-506557 | 3/2012 |
| JP | 2015-506557 | 3/2012 |
| KR | 100442838 | 7/2004 |
| KR | 100442838 | 8/2004 |
| KR | 100455283 | 10/2004 |
| KR | 100455283 | 11/2004 |
| TW | 200946904 | 11/2009 |
| WO | 89/09283 | 10/1989 |
| WO | WO-89/09283 | 10/1989 |
| WO | 1990/005910 | 5/1990 |
| WO | 98/13523 | 4/1998 |
| WO | WO-98/13523 | 4/1998 |
| WO | WO-98/46797 | 10/1998 |
| WO | 01/20039 | 3/2001 |
| WO | WO-01/20039 | 3/2001 |
| WO | 01/42498 | 6/2001 |
| WO | 01/47804 | 7/2001 |
| WO | 01/81896 | 11/2001 |
| WO | WO-01/81896 | 11/2001 |
| WO | 02/077287 | 10/2002 |
| WO | 02/086162 | 10/2002 |
| WO | WO-02/077287 | 10/2002 |
| WO | WO-02/086162 | 10/2002 |
| WO | 03/073088 | 9/2003 |
| WO | WO-03/073088 | 9/2003 |
| WO | 2004/017068 | 2/2004 |
| WO | WO-2004/040291 | 5/2004 |
| WO | WO2004040291 | 5/2004 |
| WO | WO2004048962 | 6/2004 |
| WO | WO-2004081234 | 9/2004 |
| WO | WO2005015156 | 2/2005 |
| WO | 2005/022142 | 3/2005 |
| WO | WO-2005/047878 | 5/2005 |
| WO | WO2005043160 | 5/2005 |
| WO | WO-2005/054431 | 6/2005 |
| WO | 2005/062049 | 7/2005 |
| WO | WO2005602049 | 7/2005 |
| WO | 2005/073706 | 8/2005 |
| WO | 2005090961 | 9/2005 |
| WO | WO-2005/084367 | 9/2005 |
| WO | WO2005090961 | 9/2005 |
| WO | WO-2006/005967 | 1/2006 |
| WO | WO-2006/022370 | 3/2006 |
| WO | 2006/056226 | 6/2006 |
| WO | 2007/002204 | 1/2007 |
| WO | WO2007002204 | 1/2007 |
| WO | WO-2007/086935 | 8/2007 |
| WO | WO-2008/007716 | 1/2008 |
| WO | WO-2008/058282 | 5/2008 |
| WO | 2008076406 | 6/2008 |
| WO | WO-2008/076406 | 6/2008 |
| WO | WO-2008/107014 | 9/2008 |
| WO | 2009/014155 | 1/2009 |
| WO | WO-2009/012112 | 1/2009 |
| WO | WO2009041917 | 4/2009 |
| WO | WO2009074926 | 6/2009 |
| WO | WO2009081890 | 7/2009 |
| WO | WO-2009/158006 | 12/2009 |
| WO | WO-2010/008480 | 1/2010 |
| WO | WO-2010/047804 | 4/2010 |
| WO | 2010/138186 | 12/2010 |
| WO | 2010/138188 | 12/2010 |
| WO | WO-2010/138182 | 12/2010 |
| WO | WO-2012/003359 | 1/2012 |
| WO | WO-2012/003363 | 1/2012 |
| WO | WO-2012/003368 | 1/2012 |
| WO | WO-2012/003380 | 1/2012 |
| WO | WO-2012/006222 | 1/2012 |
| WO | 2012/046137 | 4/2012 |
| WO | 2012/152308 | 11/2012 |

OTHER PUBLICATIONS

EP13174555.6 EP Search Report Nov. 21, 2013.
EP13177039.8 EP Search Report Nov. 21, 2013.
EP13177590.0 EP Search Report Nov. 20, 2013.
Hammond, et al., "Performance and System-On-Chip Integration of an Unmodified CMOS ISFET", Science Direct, Sensors and Actuators vol. 111-112, 2005, pp. 254-258.
Ingebrandt, Sven et al., "Label-free Detection of DNA using Field-Effect Transistors", Phys. stat. sol. (a) 203, No. 14, 2006, pp. 3399-3411.
Wood, et al. "Base composition-independent hybridization in tetramethylammonium chloride: a method for oligonucleotide screening of highly complex gene libraries" Proc. Nat. Acad. Sci., 1985, pp. 1585-1588.
EP14152861.2 EP Search Report date Jul. 7, 2014.
Palan, B. et al., "New ISFET sensor interface circuit for biomedical applications", Sensors and Actuators B: Chemical: International Journal Devoted to Research and Development of Physical and Chemical Transducers, Elsevier S.A. Ch., vol. 57, No. 1-3, 1999, pp. 63-68.
PCT/US2013/022129 International Preliminary Report on Patentability dated Jul. 22, 2014.
PCT/US2013/022140 International Preliminary Report on Patentability dated Jul. 22, 2014.
Zhao, B. et al., "Floating-Gate Ion Sensitive Field-Effect Transistor for Chemical and Biological Sensing", MRS Proceedings, vol. 828, 2004, pp. 349-354.
Bockelmann, U. et al., "Detecting DNA by field effect transistor arrays", *Proceedings of the 2006 IFIP International Conference on Very Large Scale Integration*, 2006, 164-168.
EP11801439.8 EP Extended Search Report dated Mar. 7, 2014.
Tokuda, T. et al., "A CMOS image sensor with optical and potential dual imaging function for on-chip bioscientific applications", *Sensors and Actuators A*, vol. 125, No. 2, 2006, 273-280.
[No Author Listed], "ISFET Wikipedia article", Wikipedia, Last modified Nov. 7, 2006.
Akiyama, T. et al., "Ion-Sensitive Field-Effect Transistors with Inorganic Gate Oxide for pH Sensing", IEE Transactions on Electron Devices, vol. ED-29 (12), 1982, pp. 1936-1941.
AU2011226767 Search Information Statement Mailed Oct. 26, 2011.
Bandiera, L. et al., "A fully electronic sensor for the measurement of cDNA hybridization kinetics", Biosens Bioelectron, vol. 22, 2007, pp. 2108-2114.

(56) References Cited

OTHER PUBLICATIONS

Barbaro, M. et al., "A CMOS, Fully Integrated Sensor for Electronic Detection of DNA Hybridization", IEEE Electron Device Letters, vol. 27(7), 2006, pp. 595-597.
Barbaro, M. et al., "A Charge-Modulated FET for Detection of Biomolecular Processes: Conception, Modeling, and Simulation", IEEE Transactions on Electron Devices, vol. 53(1), 2006, pp. 158-166.
Barbaro, M. et al., "Fully electronic DNA hybridization detection by a standard CMOS biochip", Sensors and Actuators B Chemical, vol. 118, 2006, pp. 41-46.
Bashford, G. et al., "Automated bead-trapping apparatus and control system for single-molecule DNA sequencing", Optics Express, vol. 16(5), 2008, pp. 3445-3455.
Baumann, W. et al., "Microelectronic sensor system for microphysiological application on living cells", Sensors and Actuators B, vol. 55(1), 1999, pp. 77-89.
Bausells, J. et al., "Ion-sensitive field-effect transistors fabricated in a commercial CMOS technology", Sensors and Actuators B Chemical, vol. 57(1-3), 1999, pp. 56-62.
Bergveld, P., "ISFET, Theory and Practice", IEEE Sensor Conference, Toronto, Oct. 2003, 2003, pp. 1-26.
Bergveld, P., "Thirty years of ISFETOLOGY What happened in the past 30 years and what may happen in the next 30 years", Sensors and Actuators B, vol. 88(1), 2003, pp. 1-20.
Besselink, G. et al., "ISFET Affinity Sensor", Methods in Biotechnology, vol. 7: Affinity Biosensors: Techniques and Protocols, 1998, pp. 173-185.
Bobrov, P. et al., "Chemical sensitivity of an ISFET with $Ta_2O_5$ membrane in strong acid and alkaline solutions", Sensors and Actuators B, vol. 3, 1991, pp. 75-81.
Bousse, L. et al., "A process for the combined fabrication of ion sensors and CMOS circuits", IEEE Electron Device Letters, vol. 9(1), 1988, pp. 44-46.
Bousse, L. et al., "Zeta potential measurements of $Ta_2O_5$ and $SiO_2$ thin films", J. Colloid Interface Sci., vol. 147(1), 1991, pp. 22-32.
Chan, Wai P. et al., "An Integrated ISFETs Instrumentation System in Standard CMOS Technology", IEEE Journal of Solid-State Circuits, vol. 45, No. 9, 2010, pp. 1923-1934.
Chen, Y. et al., "Nanoscale field effect transistor for biomolecular signal amplification", App Phys Letter, vol. 91(24), 2007, pp. 243511-1-243511-3.
Chen, Y. et al., "Silicon-based nanoelectronic field-effect pH sensor with local gate control", App Phys Letter, vol. 89, 2006, pp. 223512-1-223512-3.
Chinese Patent Application 200780051353.2 Second Office Action Mailed Mar. 5, 2013.
Chou, J. et al., Letter to the Editor on "Simulation of Ta2O5 gate ISFET temperature characteristics", Sensors and Actuators B, vol. 80, 2001, pp. 290-291.
Chou, J. et al., "Simulation of Ta2O5 gate ISFET temperature characteristics", Sensor and Actuators B, vol. 71, Letter to the Editor, 2000, pp. 73-76.
Chung, W-Y. et al., "ISFET interface circuit embedded with noise rejection capability", Electronics Letters, vol. 40(18), e-pub, 2004, 1115-1116.
Chung, W-Y. et al., "ISFET performance enhancement by using the improved circuit techniques", Sensors and Actuators B, vol. 113, 2006, pp. 555-562.
Chung, W-Y. et al., "New ISFET Interface Circuit Design with Temperature Compensation", Microelectronics Journal, vol. 37(10), 2006, pp. 1105-1114.
Chung, W-Y. et al., "Temperature Compensation Electronics for ISFET Readout Applications", Biomedical Circuits and Systems, IEEE International Workshop Singapore, 2004, pp. 305-308.
Eijkel, J. et al., "Measuring Donnan-related phenomena using a solid-state ion sensor and a concentration-step method", J. Membrane Sci., vol. 127, 1997, pp. 203-221.

Eijkel, J., "Potentiometric detection and characterization of adsorbed protein using stimulus-response measurement techniques", Thesis, Sep. 3, 1955, pp. 1 -147; 160-192.
Eltoukhy, H. et al., "A 0.18um CMOS 10-6 lux Bioluminescence Detection System-on-Chip", ISSCC 2004/Session12/Biomicrosystems/12.3, 2004, pp. 1-3.
Eltoukhy, H. et al., "A. 0.18-um CMOS Bioluminescence Detection Lab-on-Chip", IEEE J Solid-State Circuits, vol. 41(3), 2006, pp. 651-662.
EP7867780.4 Examination Report Mailed Jul. 3, 2012.
Esfandyarpour, H. et al., "Gate-controlled microfluidic chamber with magnetic bead for DNA sequencing-by-synthesis technology", Proc 5th Intl Conf Nanochannels, Microchannels and Minichannels, Puebla, Mexico, Jun. 18-20, 2007, pp. 1-5.
Eversmann, B. et al., "A 128 ×128 CMOS Biosensor Array for Extracellular Recording of Neural Activity", IEEE J. Solid-State Circ., vol. 38(12), 2003, pp. 2306-2317.
Faramarzpour, N. et al., "CMOS-Based Active Pixel for Low-Light Level Detection: Analysis and Measurements", IEEE Trans Electron Devices, vol. 54(12), 2007, pp. 3229-3237.
Finn, A. et al., "Towards an Optimization of FET-Based Bio-Sensors", European Cells and Materials, vol. 4, Sup 2, 2002, pp. 21-23.
Fraden, J., "Handbook of Modern Sensors-Physics, Designs, and Applications", 17.3.2 CHEMFET Sensors, 1996, pp. 499-501.
Fritz, J. et al., "Electronic detection of DNA by its intrinsic molecular charge", PNAS, vol. 99(22), 2002, pp. 14142-14146.
GB0811656.8 Search and Examination Report Mailed Mar. 12, 2010.
GB0811656.8 Search Report Mailed Sep. 21, 2009.
GB0811657.6 Examination Report Mailed Jun. 30, 2010.
GB0811657.6 Search Report under Section 17 Mailed Oct. 26, 2009.
Gracia, I. et al., "Test Structures for ISFET Chemical Sensors", Proc IEEE 1992 Intl Conf Microelec Test Struct, 1992, pp. 156-159.
Hammond, P. et al., "A System-on-Chip Digital pH Meter for Use in a Wireless Diagnostic Capsule", IEEE Trans Biomedical Eng., vol. 52(4), 2005, pp. 687-694.
Hammond, P. et al., "Design of a Single-Chip pH Sensor Using a Conventional 0.6-µm CMOS Process", IEEE Sensors Journal, vol. 4(6), 2004, pp. 706-712.
Hammond, P. et al., "Encapsulation of a liquid-sensing microchip using SU-8 photoresist", MicoElectronic Engineering, vol. 73-74, 2004, pp. 893-897.
Hammond, S. et al., "Genomic sequencing and analysis of a Chinese Hamster ovary cell line using Illumine sequencing technology", BMC Genomics, vol. 12:67, 2011, pp. 1-8.
Han, Y., "Label-free detection of biomolecules by a field-effect transistor microarray biosensor with bio-functionalized gate surfaces", Aachen, Techn. Hochsch., Diss., 2006, pp. 1-63.
Hara, H. et al., "Dynamic response of a $Ta_2O_5$-gate pH-sensitive field-effect transistor", Sensors Actuators B, vol. 32, 1996, pp. 115-119.
Hermon, Z. et al., "Miniaturized bio-electronic hybrid for chemical sensing applications", Tech Connect News, 2008, p. 1.
Hideshima, S. et al., "Detection of tumor marker in blood serum using antibody-modified field effect transistor with optimized BSA blocking", Sensors and Actuations B: Chemical, vol. 161, 2012, pp. 146-150.
Hizawa, T. et al., "Fabrication of a two-dimensional pH image sensor using a charge transfer technique", Sensors and Actuators B Chemical, vol. 117, 2006, pp. 509-515.
Hizawa, T. et al., "32 × 32 pH Image Sensors for Real Time Observation of Biochemical Phenomena", Solid-State Sensors, Actuators and Microsystems Conference, 2007, Transducers 2007. International, 2007, pp. 1311-1312.
Jakobson, C. et al., "Low frequency noise and drift in Ion Sensitive Field Effect Transistors", Sensors Actuators B, vol. 68, 2000, pp. 134-139.
Ji, H. et al., "A CMOS contact imager for locating individual cells", ISCAS, 2006, pp. 3357-3360.

(56) References Cited

OTHER PUBLICATIONS

Ji, H. et al., "Contact Imaging: Simulation and Experiment", IEEE Trans Circuits Systems-I: Regular Papers, vol. 54(8), 2007, pp. 1698-1710.
Kim, D. et al., "An FET-type charger sensor for highly sensitive detection of DNA sequence", Biosens Bioelectron, vol. 20(1), 2004, pp. 69-74.
Klein, M., "Time effects of ion-sensitive field-effect transistors", Sensors and Actuators B, vol. 17(1-2), 1989, pp. 203-208.
Koch, S. et al., "Protein detection with a novel ISFET-based zeta potential analyzer", Biosensors & Bioelectronics, vol. 14, 1999, pp. 413-421.
Krause, M. et al., "Extended Gate Electrode Arrays for Extracellular Signal Recordings", Sensors and Actuators B, vol. 70, 2000, pp. 101-107.
Kruise, J. et al., "Detection of protein concentrations using a pH-step titration method", Sensors Actuators B, vol. 44, 1997, pp. 297-303.
Leamon, J. et al., "A Massively Parallel PicoTiterPlate Based Platform for Discrete Picoliter-Scale Polymerase Chain Reactions", Electrophoresis, vol. 24, 2003, pp. 3769-3777.
Leamon, J. et al., "Cramming More Sequencing Reactions onto Microreactor Chips", Chemical Reviews, vol. 107, 2007, pp. 3367-3376.
Lee, C-S. et al., "Ion-sensitive Field-Effect Transistor for Biological Sensing", Sensors, vol. 9, 2009, pp. 7111-7131.
Lohrengel, M. et al., "A new microcell or microreactor for material surface investigations at large current densities", Electrochimica Acta, vol. 49, 2004, pp. 2863-2870.
Lui, A. et al., "A Test Chip for ISFET/CMNOS Technology Development", Proc. of the 1996 IEEE Intl. Conf. on Microelectronic Test Structures, vol. 9, 1996, pp. 123-128.
Margulies, M. et al., "Genome sequencing in microfabricated high-density picolitre reactors", Nature, vol. 437(7057), 2005, pp. 376-380.
Marshall, A. et al., "DNA chips: an array of possibilities", Nature Biotechnology, vol. 16, 1998, pp. 27-31.
Martinoia, S. et al., "A behavioral macromodel of the ISFET in SPICE", Sensors Actuators B, vol. 62, 2000, pp. 182-189.
Martinoia, S. et al., "Development of ISFET Array-Based Microsystems for Bioelectrochemical measurements of cell populations", Biosensors & Bioelectronics, vol. 16, 2001, pp. 1043-1050.
Medoro, G. et al., "A Lab-on-a-Chip for Cell Detection and Manipulation", IEEE Sensors J, vol. 3(3), 2003, pp. 317-325.
Meyburg, S. et al., "N-Channel field-effect transistors with floating gates for extracellular recordings", Biosens Bioelectron, vol. 21(7), 2006, pp. 1037-1044.
Milgrew, M. et al., "A 16×16 CMOS proton camera array for direct extracellular imaging of hydrogen-ion activity", IEEE Intl Solid-State Circuits Conf, Session 32:24, 2008, pp. 590-638.
Milgrew, M. et al., "A large transistor based sensor array chip for direct extracellular imaging", Sensors and Actuators B Chemical, vol. 111-112, 2005, pp. 347-353.
Milgrew, M. et al., "Matching the transconductance characteristics of CMOS ESFET arrays by removing trapped charge", IEEE Trans Electron Devices, vol. 55(4), 2008, pp. 1074-1079.
Milgrew, M. et al., "Microsensor Array Technology for Direct Extracellular Imaging", Dept Electronic and EE, University of Glasgow, 2006, pp. 1-23.
Milgrew, M. et al., "The development of scalable sensor arrays using standard CMOS technology", Sensors and Actuators B, vol. 103, 2004, pp. 37-42.
Milgrew, M. et al., "The fabrication of scalable multi-sensor arrays using standard CMOS technology", 2003 IEEE Custom Integrated Circuits Conference, 2003, pp. 513-516.
Miyahara, Y. et al., "Biochip Using Micromachining Technology", J. Institute of Electrostatics, Japan, vol. 27(6), (Translation Included), 2003, pp. 268-272.
Miyahara, Y. et al., "Direct Transduction of Primer Extension into Electrical Signal Using Genetic Field Effect Transistor", Micro Total Analysis Systems 2004, vol. 1, 2004, pp. 303-305.
Miyahara, Y. et al., "Potentiometric Detection of DNA Molecules Using Field Effect Transistor", The Japan Society of Applied Physics, No. 3 (Translation included), 2003, pp. 1180.
Nyren, P. et al., "Enzymatic Method for Continuous Monitoring of Inorganic Pyrophosphate Synthesis", Analytical Biochemistry, vol. 151, 1985, pp. 504-509.
Oelbner, W. et al., "Encapsulation of ESFET sensor chips", Sensors Actuators B, vol. 105, 2005, pp. 104-117.
Oelbner, W. et al., "Investigation of the dynamic response behaviour of ISFET pH sensors by means of laser Doppler velocimetry (LDV)", Sensors Actuators B, vol. 26-27, 1995, pp.345-348.
Offenhausser, A. et al., "Field-Effect transistor array for monitoring electrical activity from mammalian neurons in culture", Biosensors & Bioelectronics, vol. 12(8), 1997, pp. 819-826.
Ohno, Y. et al., "Electrolyte-Gated Graphene Field-Effect Transistors for Detecting pH and Protein Adsorption", Nano Letters, vol. 9(9), Jul. 28, 2009, pp. 3318-3322.
Park, K-Y. et al., "ISFET Glucose Sensor System With Fast Recovery Characteristics by Employing Electrolysis", Sensors and Actuators B: Chemical, vol. 83 (1-3), 2002, pp. 90-97.
Patolsky, F. et al., "Nanowire-Based Biosensors", Analyt Chem 1, vol. 78(13), 2006, pp. 4261-4269.
PCT/US2009/05745 International Preliminary Report on Patentability Mailed Apr. 26, 2011.
PCT/US2009/05745 International Search Report Mailed Dec. 11, 2009.
PCT/US2009/05745 Written Opinion Mailed Dec. 11, 2009.
PCT/US2007/025721 International Preliminary Report on Patentability Mailed Jun. 16, 2009.
PCT/US2007/025721 Written Opinion Mailed Jun. 16, 2009.
PCT/US2009/003766 International Preliminary Report on Patentability Mailed Jan. 5, 2011.
PCT/US2009/003766 International Search Report Mailed Apr. 8, 2010.
PCT/US2009/003766 Written Opinion Mailed Apr. 8, 2010.
PCT/US2009/003797 International Search Report Mailed Mar. 12, 2010.
PCT/US2009/003797 Written Opinion Mailed Mar. 12, 2010.
PCT/US2010/001543 International Preliminary Report on Patentability Mailed Nov. 29, 2011.
PCT/US2010/001543 International Search Report and Written Opinion Mailed Oct. 13, 2010.
PCT/US2010/048835 International Preliminary Report on Patentability Mailed Mar. 19, 2013.
PCT/US2010/048835 International Search Report and Written Opinion Mailed Dec. 16, 2010.
PCT/US2011/042655 International Search Report Mailed Oct. 21, 2011.
PCT/US2011/042660 International Search Report Mailed Nov. 2, 2011.
PCT/US2011/042665 International Search Report Mailed Nov. 2, 2011.
PCT/US2011/042668 International Preliminary Report on Patentability Mailed Mar. 26, 2013.
PCT/US2011/042668 International Search Report Mailed Oct. 28, 2011.
PCT/US2011/042669 International Search Report Mailed Jan. 9, 2012.
PCT/US2011/042669 Written Opinion Mailed Jan. 9, 2012.
PCT/US2011/042683 International Search Report Mailed Feb. 16, 2012.
PCT/US2011/042683 Written Opinion Mailed Feb. 16, 2012.
PCT/US2012/058996 International Search Report and Written Opinion Mailed Jan. 22, 2013.
PCT/US2012/071471 International Search Report and Written Opinion Mailed Apr. 24, 2013.
PCT/US2012/071482 International Search Report and Written Opinion Mailed May 23, 2013.
PCT/US2013/022140 International Search Report and Written Opinion Mailed May 2, 2013.

(56) References Cited

OTHER PUBLICATIONS

Poghossian, A. et al., "Functional testing and characterization of ISFETs on wafer level by means of a micro-droplet cell", Sensors, vol. 6, 2006, pp. 397-404.

Pollack, J. et al., "Genome-Wide Analysis of DNA copy-number changes using cDNA Microarrays", Nature Genetics, vol. 23, 1999, pp. 41-46.

Pourmand, N. et al., "Direct electrical detection of DNA synthesis", PNAS, vol. 103(17), 2006, pp. 6466-6470.

Pouthas, F. et al., "Spatially resolved electronic detection of biopolymers", Phys Rev, vol. 70, 2004, pp. 031906-1-031906-8.

Premanode, B. et al., "A composite ISFED readout circuit employing current feedback", Sensors Actuators B, vol. 127, 2007, pp. 486-490.

Premanode, B. et al., "A novel, low power biosensor for real time monitoring of creatine and urea in peritoneal dialysis", Sensors Actuators B, vol. 120, 2007, pp. 732-735.

Premanode, B. et al., "Ultra-low power precision ISFET readout using global current feedback", Electronic Lett, vol. 42(22), 2006, pp. 1264-1265.

Purushothaman, S. et al., "Protons and single nucleotide polymorphism detection: A simple use for the Ion Sensitive Field Effect Transistor", Sensors and Actuators B Chemical, vol. 114(2), 2006, pp. 964-968.

Purushothaman, S. et al., "Towards Fast Solid State DNA Sequencing", IEEE ISCAS 2002 Proceedings, Circuits and Systems, vol. 4, 2002, pp. IV-169-IV-172.

Rodriguez-Villegas, E., "Solution to trapped charge in FGMOS transistors", Electronics Letters, vol. 39(19), 2003.

Sakata, T. et al., "Cell-based field effect devices for cell adhesion analysis", Intl. Conf. on Microtechnologies in Medicine and Biology, May 9-12, 2006, Okinawa, Japan, pp. 177-179.

Sakata, T. et al., "Detection of DNA recognition events using multi-well field effect transistor", Biosensors and Bioelectronics vol. 21, 2005, pp. 827-832.

Sakata, T. et al., "Detection sensitivity of genetic field effect transistor combined with charged nanoparticle-DNA conjugate", Proc. of 2006 Intl. Conf. on Microtechnologies in Medicine and Biology, May 9-12, 2006, Okinawa, Japan, pp. 97-100.

Sakata, T. et al., "Direct detection of single nucleotide polymorphism using genetic field effect transistor", Digest of Papers Microprocesses and Nanotechnology 2004, Osaka, Japan, 2004 International Microprocesses and Nanotechnology Conference, 2004, pp. 226-227.

Sakata, T. et al., "Direct Detection of Single-Base Extension Reaction Using Genetic Field Effect Transistor", Proc. of 3rd Ann. Intl. IEEE EMBS Special Topic Conf. on Microtechnologies in Medicine and Biology, Kahuku, Oahu, HI, May 12-15, 2005, pp. 219-222.

Sakata, T. et al., "Direct transduction of allele-specific primer extension into electrical signal using genetic field effect transistor", Biosensors and Bioelectronics, vol. 22, 2007, pp. 1311-1316.

Sakata, T. et al., "DNA Analysis Chip Based on Field-Effect Transistors", Japanese Journal of Applied Physics, vol. 44(4B), 2005, pp. 2854-2859.

Sakata, T. et al., "DNA Sequencing Based on Intrinsic Molecular Charges", Angewandte Chemie International Edition 2006, vol. 118, 2006, pp. 2283-2286.

Sakata, T. et al., "DNA Sequencing Based on Intrinsic Molecular Charges", Angewandte Chemie International Edition 2006, vol. 45, 2006, pp. 2225-2228.

Sakata, T. et al., "DNA Sequencing Using Genetic Field Effect Transistor", Solid-State Sensors, Actuators and Microsystems, vol. 2, 2005, pp. 1676-1679.

Sakata, T. et al., "Immobilization of oligonucleotide probes on Si3N4 surface and its application to genetic field effect transistor", Materials Science and Engineering: C, vol. 24, 2004, pp. 827-832.

Sakata, T. et al., "Potential Behavior of Biochemically Modified Gold Electrode for Extended-Gate Field-Effect Transistor", Japanese Journal of Applied Physics, vol. 44(4B), 2005, pp. 2860-2863.

Sakata, T. et al., "Potential Response of Genetic Field Effect Transistor to Charged Nanoparticle-DNA Conjugate", Digest of Papers Microprocesses and Nanotechnology 2005, Tokyo, Japan, 2005 Intl Microprocesses and Nanotech Conf., Hotel Bellclassic, 2005, pp. 42-43.

Sakata, T. et al., "Potentiometric Detection of Allele Specific Oligonucleotide Hybridization Using Genetic Field Effect Transistor", Micro Total Analysis Systems, 8th Intl. Conf. on Miniaturized Systems for Chemistry and Life Sciences, 2004, pp. 300-302.

Sakata, T. et al., "Potentiometric detection of DNA molecules hybridization using gene field effect transistor and intercalator" Materials Research Society Symposium Proceedings, vol. 782, 2004, pp. 393-400.

Sakata, T. et al., "Potentiometric Detection of DNA Using Genetic Transistor", Denki Gakkai Kenkyukai Shiryo Chemical Sensor Kenkyukai, CHS-03-51-55, 2003, pp. 1-5.

Sakata, T. et al., "Potentiometric Detection of Single Nucleotide Polymorphism by Using a Genetic Field-effect transistor", ChemBioChem, vol. 6, 2005, pp. 703-710.

Sakurai, T. et al., "Real-Time Monitoring of DNA Polymerase Reactions by a Micro ISFET pH Sensor", Anal Chem, vol. 64(17), 1992, pp. 1996-1997.

Salama, K., "CMOS luminescence detection lab-on-chip: modeling, design, and characterization", Thesis, Presented at Stanford University, 2005, pp. ii-78.

Salama, K., "Modeling and simulation of luminescence detection platforms", Biosensors & Bioelectronics, 2004, pp. 1377-1386.

Sawada, K. et al., "A novel fused sensor for photo- and ion-sensing", Sensors Actuators B, vol. 106, 2005, pp. 614-618.

Sawada, K. et al., "Highly sensitive ion sensors using charge transfer technique", Sensors Actuators B, vol. 98, 2004, pp. 69-72.

Schasfoort, R. et al., "A new approach to immunoFET operation", Biosensors & Bioelectronics, vol. 5, 1990, pp. 103-124.

Schasfoort, R. et al., "Field-effect flow control for microfabricated fluidic networks", Science, vol. 286(5441), 1999, pp. 942-945.

Schoning, M. et al., "Bio FEDs (Field-Effect Devices): State-of-the-Art and New Directions", Electroanalysis, vol. 18(19-20), 2006, pp. 1893-1900.

SG200903992-6 Search and Examination Report Mailed Jan. 20, 2011.

Shah, N., "Microfabrication of a parellel-array DNA pyrosequencing chip", NNIN REU Research Accomplishments, 2005, pp. 130-131.

Shepherd, L. et al., "A biochemical translinear principle with weak inversion ISFETs", IEEE Trans Circuits Syst-I, vol. 52(12), 2005, pp. 2614-2619.

Shepherd, L. et al., "A novel voltage-clamped CMOS ISFET sensor interface", IEEE, 2007, pp. 3331-3334.

Shepherd, L. et al., "Towards direct biochemical analysis with weak inversion ISFETS", Intl Workshop on Biomedical, 2004, S1.5-5-S1.5-8.

Shepherd, L. et al., "Weak inversion ISFETs for ultra-low power biochemical sensing and real-time analysis", Sensors Actuators B, vol. 107, 2005, pp. 468-473.

Shi, Y. et al., "Radical Capillary Array Electrophoresis Microplace and Scanner for High-Performance Nucleic Acid Analysis", Anal. Chem., vol. 71(23), 1999, pp. 5354-5361.

Simonian, A. L. et al., "FET based biosensors for the direct detection of organophosphate neurotoxins", Electroanalysis, vol. 16(22), 2004, pp. 1896-1906.

Souteyrand, E. et al., "Direct detection of the hybridization of synthetic homo-oligomer DNA sequences by field effect", J Phys Chem B, vol. 101(15), 1997, pp. 2980-2985.

Starodub, N. et al., "Immunosensor for the determination of the herbicide simazine based on an ion-selective field-effect transistor", Analytica Chimica Acta, vol. 424, 2000, pp. 37-43.

Takenaka, S. et al., "DNA Sensing on a DNA Probe-Modified Electrode Using Ferrocenylnaphthalene Dimide as the Electrochemically Active Ligand", Anal. Chem., vol. 72(6), 2000, pp. 1334-1341.

Tomaszewski, D. et al., "Electrical characterization of ISFETs", J Telecomm Info Technol, 2007, pp. 55-60.

(56) References Cited

OTHER PUBLICATIONS

Toumazou, C. et al., "Using transistors to linearase biochemistry", Elect Let, vol. 43(2), 2007, p. 3.
Truman, P. et al. "Monitoring liquid transport and chemical composition in lab on a chip systems using ion sensitive FET devices", Lab on a Chip, vol. 6, 2006, pp. 1220-1228.
Uslu, F. et al., "Labelfree fully electronic nucleic acid detection system based on a field-effect transistor device", Biosens & Bioelectron, vol. 19(12), 2004, pp. 1723-1731.
Van Der Wouden, E. et al., "Directional flow induced by synchronized longitudinal and zeta-potential controlling AC-electrical fields", Lab Chip, vol. 6(10), 2006, pp. 1300-1305.
Van Hal, R.E.G. et al., "A general model to describe the electrostatic potential at electrolyte oxide interfaces", Advances in Colloid and Interface Science, vol. 69, 1996, pp. 31-62.
Van Kerkhof, J. et al., "ISFET Responses on a stepwise change in electrolyte concentration at constant pH", Sensors Actuators B: Chemical, vol. 18-19, 1994, pp. 56-59.
Van Kerkhof, J. et al., "The ISFET based heparin sensor with a monolayer of protamine as affinity ligand", Biosensors & Bioelectronics, vol. 10(3), 1995, pp. 269-282.
Van Kerkhof, J., "Development of an ISFET based heparin sensor using the ion-step measuring method", Biosensors and Bioelectronics, 8 (9-10). pp. 463-472.
Wagner, T. et al., "All-in-one solid-state device based on a light-addressable potentiometric sensor platform", Sensors and Actuators B, vol. 117, 2006, pp. 472-479.
Wang, W. et al., "Label-free detection of small-molecule-protein interactions by using nanowire nanosensors", Proc. of the Natl. Acad.of Sciences (PNAS), vol. 102(9), 2005, pp. 3208-3212.
Woias, P. et al., "Slow pH response effects of silicon nitride ISFET sensors", Sensors and Actuators B, vol. 48, 1998, pp. 501-504.
Woias, P., "Modeling the short time response of ISFET sensors", Sensors and Actuators B, vol. 24-25, 1995, pp. 211-217.
Wu, P. et al., "DNA and protein microarray printing on silicon nitride waveguide surfaces", Biosensens Bioelectron, vol. 21(7), 2006, pp. 1252-1263.
Xu, J. et al., "Analytical Aspects of FET-Based Biosensors", Frontiers in Bioscience, vol. 10, 2005, pp. 420-430.
Yeow, T.C.W. et al., "A very large integrated pH-ISFET sensor array chip compatible with standard CMOS processes", Sensor and Actuators B, vol. 44, 1997, pp. 434-440.
Yuqing, M. et al., "Ion sensitive field effect transducer-based biosensors", Biotechnology Advances, vol. 21, 2003, pp. 527-534.
Zhang, X. et al., "32-Channel Full Customized CMOS Biosensor Chip for Extracellular neural Signal Recording", Proc. of the 2nd Intl. IEEE EMBs Conf. on Neural Engineering, Arlington, Virginia, 2005, pp. v-viii.
Zhou, G. et al., "Quantitative detection of single nucleotide polymorphisms for a pooled sample by a bioluminometric assay coupled with modified primer extension reactions (BAMPER)", Nuc. Acids Res., vol. 29(19), e93, 2001, pp. 1-11.
Dazhong, Z. et al. "Research of CMOS Biosensor IC for Extracellular Electrophysiological Signal Recording and pH value Measuring" Solid-State and Integrated Circuit Technology, 9th International Conference, Oct. 20, 2008, pp. 2557-2560.
EP11801437.2 Extended European Search Report dated Jul. 25, 2013.
EP11804218.3 Extended European Search Report dated Jul. 11, 2013.
EP11804218.3 First Office Action dated Jul. 29, 2013.
EP11827128.7 European Search Report dated Aug. 1, 2013.
EP13161312.7 Extended European Search Report dated Oct. 15, 2013.
EP13163995.7 Extended European Search Report dated Aug. 20, 2013.
Eriksson, J. et al. "Pyrosequencing Technology at Elevated Temperature" Electrophoresis, vol. 25, 2004, pp. 20-27.
Hanshaw, R. et al., "An indicator displacement system for fluorescent detection of phosphate oxyanions under physiological conditions" Science Direct, Tetrahedron Ltrs., vol. 45, 2004, pp. 8721-8724.
Hizawa, et al. "Sensing Characteristics of Charge Transfer Type pH Sensor by Accumulative Operation" IEEE Sensors, EXCO, Daegu, Korea, 2006, pp. 144-147.
JP20120246413 First Office Action dated Jun. 28, 2013.
Lee, S. et al. "An Enhanced Glucose Biosensor Using Charge Transfer Techniques" Biosensors and Bioelectronics, vol. 24, 2008, pp. 650-656.
Matsuo, J. et al. "Charge Transfer Type pH Sensor with Super High Sensitivity" 14th International Conference on Solid-State Sensors Actuators and Microsystems, France, Jun. 10-14, 2007, pp. 1881-1884.
Milgrew, M. et al. "A Proton Camera Array Technology for Direct Extracellular Ion Imaging" IEEE International Symposium on Industrial Electronics, 2008, pp. 2051-255.
Milgrew, M.J. et al., "The Development of Scalable Sensor Arrays Using Standard CMOS Technology" ScienceDirect, Sensors and Actuators, vol. 103, 2004, pp. 37-42.
PCT/US2011/042683 International Preliminary Report on Patentability dated Jun. 4, 2013.
PCT/US2013/022129 International Search Report and Written Opinion dated Aug. 9, 2013.
Premanode, B. et al. "Drift Reduction in Ion-Sensitive FETs Using Correlated Double Sampling", Electronics Letters, IEEE Stevenage, GB, vol. 43 (16) Aug. 2, 2007.
Rothberg, J. et al., "An integrated semiconductor device enabling non-optical genome sequencing" Nature, vol. 475, No. 7356, 2011, pp. 348-352.
Seong-Jin, K. et al. "Label-Free CMOS DNA Quantification With On-Chip Noise Reduction Schemes" Solid-State Sensors, Actuators and Microsystems Conference, IEEE, Jun. 10, 2013, pp. 947-950.
Voigt, H. et al. "Diamond-like carbon-gate pH-ISFET" Sensors and Actuators B., vol. 44, 1997, pp. 441-445.
Ahmadian, et al., "Single-nucleotide polymorphism analysis by pyrosequencing", *Anal. Biochem.* vol. 280, 2000, 103 -110.
Dorf, Richard C. , "The Electrical Engineering Handbook", *University of California, Davis, CRC Press, 2 edition, Chapter 3—Linear Circuit Analysis*, Jun. 25, 2004, pp. 3-1 to 3-66.
EP09822323.3, European Extended Search Report, May 27, 2015, 8 pages.
EP10780930, "European Search Report", Jun. 15, 2015, 3 pages.
EP10857377, "European Search Report", Jun. 26, 2015, 3 pages.
EP13163995.7, "EP Search Report mailed Jul. 9, 2014".
EP13177590.0, "European Examination Notification", Sep. 8, 2014, 9 pages.
Gardner, J.W. et al., "Enhancing electronic nose performance by sensor selection using a new integer-based genetic algorithm approach", *Science Direct, Sensors and Actuators B*, vol. 106, 2005, pp. 114-121.
Hijikata, et al., "Identification of a Single Nucleotide Polymorphism in the MXA Gene Promoter (T/T at nt-88) Correlated with the Response of Hepatitis C Patients to Interferon", *Intervirology*, vol. 43, 2000, 124-127.
Li, et al., "Sequence-Specific Label-Free DNA Sensors Based on Silico Nanowires", *Nano Letters,*, vol. 4, No. 2, 2004, 245-247.
Lin, B.J. et al., "Practicing the Novolac deep-UV portable conformable masking technique", *Journal of Vacuum Science and Technology*, Vo. 19, No. 4, 1981, 1313-1319.
Naidu, M. S. et al., "Introduction to Electrical Engineering", *Chapter 1—Fundamental Concepts of Electricity, McGraw Hill Education (India) Private Limited*, 1995, pp. 1-10.
Neaman, Donald A. , "Electronic Circuit Analysis and Design", *McGraw Hill Higher Education, 2nd edition, Chapter 6—Basic FET Amplifiers*, (reference will be uploaded in 2 parts due to size) part 1 of 2, Dec. 1, 2000, pp. 313-345.
Neaman, Donald A. , "Electronic Circuit Analysis and Design", *McGaw Hill Higher Education, 2nd edition, Chapter 6—Basic FET Amplifiers*, (reference will be uploaded in 2 parts due to size) part 2 of 2, Dec. 1, 2000, pp. 346-381.

(56) References Cited

OTHER PUBLICATIONS

Nishiguchi, K. et al., "Si nanowire ion-sensitive field-effect transistors with a shared floating gate", *Applied Physics Letters* vol. 94, 2009, pp. 163106-1 to 163106-3.
PCT/JP2005/001987, "International Search Report", Apr. 5, 2005.
PCT/JP2005/015522, "International Preliminary Report on Patentability", Mailed Mar. 19, 2007, Jul. 25, 2006.
PCT/JP2005/015522, "International Search Report", (includes English translation), Sep. 27, 2005.
PCT/US2007/025721, "Declaration of Non-Establishment of International Search Report", Jul. 15, 2008.
PCT/US2010/001553, "International Preliminary Report on Patentability", Dec. 28, 2011, pp. 1-10.
PCT/US2010/001553, "International Search Report", Jul. 28, 2010, pp. 1-2.
PCT/US2010/001553, "Written Opinion", Jul. 14, 2010, pp. 1-6.
PCT/US2014/020887, "International Search Report and Written Opinion", May 30, 2014, 12 pages.
PCT/US2014/020892, "International Search Report and Written Opinion mailed Jun. 3, 2014".
PCT/US2014/040923, "International Search Report and Written Opinion", Sep. 1, 2014, 14 pages.
Ronaghi, M. et al., "A Sequencing Method Based on Real-Time Pyrophosphate", *Science*, vol. 281, 1998, 363-365.
Temes, G.C. "A Tutorial Discussion of The Oversampling Method for A/D and D/A Conversion", *1990 IEEE International Symposium on Circuits and Systems*, vol. 2 of 4, 1990, 5 pages.
Thewes, R. et al., "CMOS-based Biosencor Arrays", *Proceedings of the Design, Automation and Test in Europe Conference and Exhibition*, 2005, 2 pages.
Van Kerkhof, , "The Development of an ISFET based heparin sensor using the ion-step measuring method", *Biosensors and Bioelectronics*, vol. 9, Nos. 9-10, 1993, 463-472.
Vardalas, John , "Twists and Turns in the Development of the Transistor", *IEEE-USA Today's Engineer Online*, May 2003, 6 pages.
Yoshida, Shoji et al., "Development of a Wide Range pH Sensor based on Electrolyte-Insulator-Semiconductor Structure with Corrosion-Resistant Al2O3—Ta2O5 and Al2O3—ZrO2", *Journal of the Electrochemical Society* vol. 151(3), 2004, pp. H53-H58.
Chin, Yuan-Lung et al., "Titanium Nitride Membrane Application to Extended Gate Field Effect Transistor pH Sensor Using VLSI Technology", *Jpn. J. Appl. Phys.* vol. 40, Part 1, No. 11, Nov. 2001, pp. 6311-6315.
International Preliminary Amendment on Patentability for International Application No. PCT/US2014/020887 mailed Sep. 15, 2015, 8 pages.
European Search Report for European Application No. EP10780935 mailed Jun. 9, 2015, 5 pages.
Supplementary European Search Report for European Application No. EP10780935 mailed Sep. 30, 2015, 6 pages.
European Search Report for European Application No. EP15170247.9 mailed Nov. 10, 2015, 4 pages.
Ligler, Frances S. et al., "Array biosensor for detection of toxins", *Anal. Bioanal Chem* vol. 377, 2003, pp. 469-477.
Matula, Richard A. , "Electrical Resistivity of Copper, Gold, Palladium, and Silver", *Journal of Physical and Chemical Reference Data*, vol. 8.4, 1979, pp. 1147-1298.
International Preliminary Report on Patentability for International Application No. PCT/US2014/040923 mailed Dec. 15, 2015, 8 pages.
Rowe, Chris A. et al., "An Array Immunosensor for Simultaneous Detection of Clinical Analytes", *Anal. Chem.* vol. 71, 1999, pp. 433-439.
Izuru, Shinmura, "Kojien", *published by Owanami, Fourth Edition*, 1991, pp. 2683.
Nakazato, Kazuo, "An Integrated ISFET Sensor Array", *SENSORS*, vol. 9, No. 11, 2009, pp. 8831-8851.
Wen-Yaw, Chung A. et al., "New ISFET interface circuit design with temperature Compensation", CiteSeerx—URL: http://citeseerx.ist.psu.edu/viewdoc/download?doi=10.1.1.95.2321&rep=re1&type=pdf, 2006, 1.
"OV5640 Datasheet Product Specification", *¼" color CMOS QSXGA (5 megapixel) image sensor with OmniBSI technology*. May 1, 2011, p. 1, line 9 and pp. 2-7, paragraph 1.
Liu, Yan et al., "An ISFET based sensing array with sensor offset compensation and pH sensitivity enhancement", *Proc. of 2010 IEEE Int. Symp. on Circuits and Systems (ISCAS)*, ISBN:978-1-4244-5308-5, Jun. 2, 2010, pp. 2283-2286.
Morgenshtein, Arkadiy et al., "Wheatstone-Bridge readout interface for ISFET/REFET applications", *Sensors and Actuators B: Chemical*, vol. 98, No. 1, Mar. 2004, pp. 18-27.
Moriizumi, Toyosaka, "Biosensors", *Oyo Buturi (monthly publication of the Japan Society of Applied Physics)*, vol. 54, No. 2, Feb. 10, 1985, pp. 98-114.
Nakazato, Kazuro et al., "28p-Y-7 ISFET sensor array integrated circuits based on standard CMOS process", *The 55th annual meeting of the Japan Society of Applied Physics, book of Abstracts*, ISBN:978-4-903968-44-5, Mar. 27, 2008, p. 70.
Nakazato, Kazuro, "An Integrated ISFET Sensor Array", *Sensors*, Nov. 2009, vol. 9, No. 11, ISSN:1424-8220, [online], Internet, URL, http://www.mdpi.com/1424-8220/9/11/8831/pdf, Nov. 2009, pp. 8831-8851.
PCT/US2015/066052, "International Search Report and Written Opinion of the International Searching Authority" dated Apr. 7, 2016, 19 pages.
Schroder, Dieter K., "6. Oxide and Interface Trapped Charges, Oxide Thickness", *Semiconductor Material and Device Characterization, John Wiley & Sons*, ISBN: 978-0-471-73906-7, Feb. 17, 2006, pp. 319-387.
PCT/US2015/066052, International Preliminary Report on Patentability, dated Jun. 29, 2017, 1-16.

* cited by examiner

METHODS FOR MANUFACTURING WELL STRUCTURES FOR LOW-NOISE CHEMICAL SENSORS

BACKGROUND

The present disclosure relates to sensors for chemical analysis, and to methods for manufacturing such sensors.

A variety of types of chemical sensors have been used in the detection of various chemical processes. One type is a chemically-sensitive field effect transistor (chemFET). A chemFET includes a source and a drain separated by a channel region, and a chemically sensitive area coupled to the channel region. The operation of the chemFET is based on the modulation of channel conductance, caused by changes in charge at the sensitive area due to a chemical reaction occurring nearby. The modulation of the channel conductance changes the threshold voltage of the chemFET, which can be measured to detect and/or determine characteristics of the chemical reaction. The threshold voltage may for example be measured by applying appropriate bias voltages to the source and drain, and measuring a resulting current flowing through the chemFET. As another example, the threshold voltage may be measured by driving a known current through the chemFET, and measuring a resulting voltage at the source or drain.

An ion-sensitive field effect transistor (ISFET) is a type of chemFET that includes an ion-sensitive layer at the sensitive area. The presence of ions in an analyte solution alters the surface potential at the interface between the ion-sensitive layer and the analyte solution, usually due to the dissociation of oxide groups by the ions in the analyte solution. The change in surface potential at the sensitive area of the ISFET affects the threshold voltage of the device, which can be measured to indicate the presence and/or concentration of ions within the solution.

Arrays of ISFETs may be used for monitoring chemical reactions, such as DNA sequencing reactions, based on the detection of ions present, generated, or used during the reactions. See, for example, U.S. Pat. No. 7,948,015 to Rothberg et al., which is incorporated by reference herein. More generally, large arrays of chemFETs or other types of chemical sensors may be employed to detect and measure static and/or dynamic amounts or concentrations of a variety of analytes (e.g. hydrogen ions, other ions, compounds, etc.) in a variety of processes. The processes may for example be biological or chemical reactions, cell or tissue cultures or monitoring, neural activity, nucleic acid sequencing, etc.

A specific issue that arises in the operation of chemical sensor arrays is the susceptibility of the sensor output signals to noise. Specifically, the noise affects the accuracy of the downstream signal processing used to determine the characteristics of the chemical and/or biological process being detected by the sensors.

It is therefore desirable to provide devices including low noise chemical sensors, and methods for manufacturing such devices.

SUMMARY

In one implementation, a method for manufacturing a chemical detection device is described. The method includes forming a chemical sensor having a sensing surface. A dielectric material is deposited on the sensing surface. A first etch process is performed to partially etch the dielectric material to define an opening over the sensing surface and leave remaining dielectric material on the sensing surface. An etch protect material is formed on a sidewall of the opening. A second etch process is then performed to selectively etch the remaining dielectric material using the etch protect material as an etch mask, thereby exposing the sensing surface.

In another implementation, a chemical detection device is described. The device includes a chemical sensor having a sensing surface. A dielectric material has an opening extending to the sensing surface. A sidewall spacer is on a sidewall of the opening. The sidewall spacer has a bottom surface spaced away from the sensing surface and an inside surface defining a reaction region for receiving at least one reactant.

Particular aspects of one more implementations of the subject matter described in this specification are set forth in the drawings and the description below. Other features, aspects, and advantages of the subject matter will become apparent from the description, the drawings, and the claims.

DETAILED DESCRIPTION

A chemical detection device is described that includes low noise chemical sensors, such as chemically-sensitive field effect transistors (chemFETs), for detecting chemical reactions within overlying, operationally associated reaction regions.

Applicants have found that a significant amount of the total noise in chemical sensors, such as chemFETs, can be attributed to etching processes involved in forming the overlying reaction regions. In particular, subjecting the sensing surface of a chemical sensor to prolonged periods of a high-energy directional etching process can cause significant noise in the sensor. For example, plasma impinging on the sensing surface can cause charge build up, to the point of causing undesirable changes or damage within the sensor. This accumulated charge can become trapped in the gate oxide and/or the gate oxide-semiconductor substrate interface of the chemFETs, thereby contributing to the noise and resulting in variations in operation and degradation in performance.

Techniques described herein can reduce or eliminate charge accumulation in the chemical sensors during the formation of the overlying reaction regions. In doing so, low noise chemical sensors with uniform performance across an array are provided, such that the characteristics of subsequent chemical reactions can be accurately detected.

Figure 1:
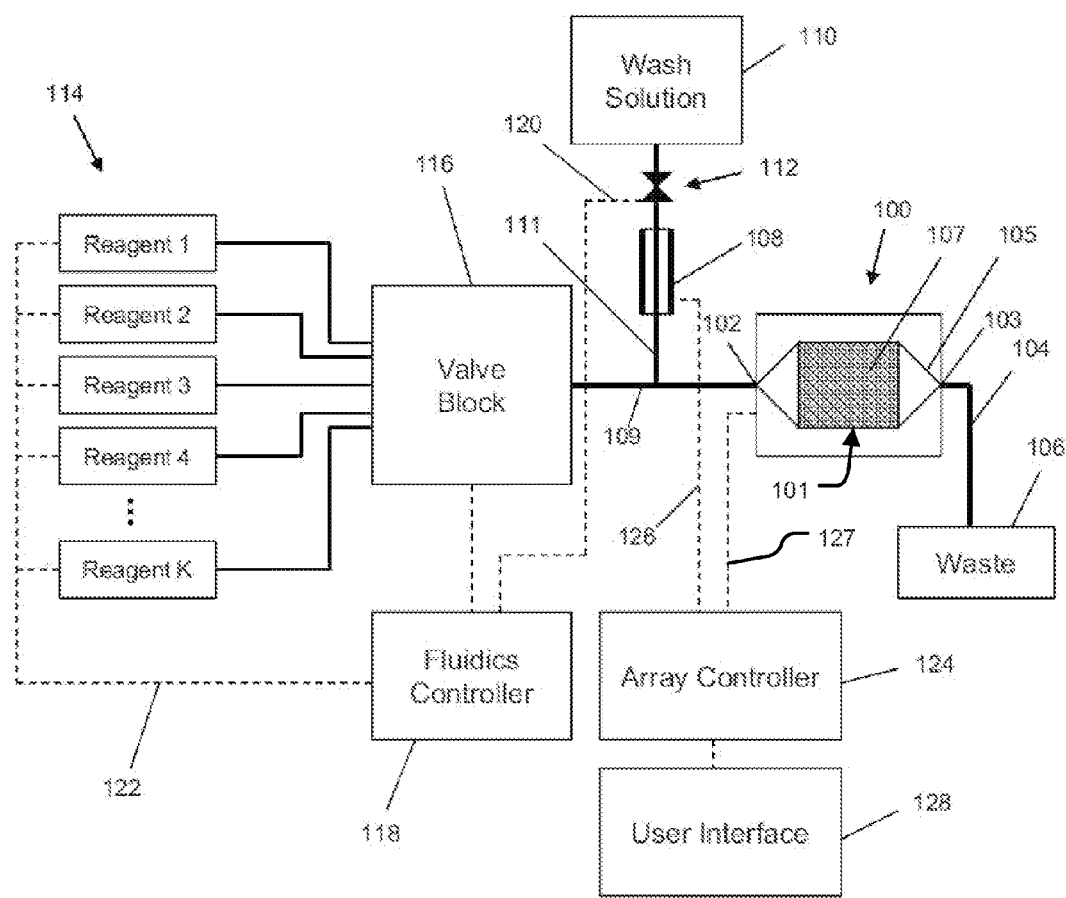
FIG. 1 illustrates a block diagram of components of a system for nucleic acid sequencing according to an exemplary embodiment.

FIG. 1 illustrates a block diagram of components of a system for nucleic acid sequencing according to an exemplary embodiment. The components include a flow cell 101 on an integrated circuit device 100, a reference electrode 108, a plurality of reagents 114 for sequencing, a valve block 116, a wash solution 110, a valve 112, a fluidics controller 118, lines 120/122/126, passages 104/109/111, a waste container 106, an array controller 124, and a user interface 128. The integrated circuit device 100 includes a microwell array 107 overlying a sensor array that includes chemical sensors as described herein. The flow cell 101 includes an inlet 102, an outlet 103, and a flow chamber 105 defining a flow path of reagents over the microwell array 107.

The reference electrode 108 may be of any suitable type or shape, including a concentric cylinder with a fluid passage or a wire inserted into a lumen of passage 111. The reagents 114 may be driven through the fluid pathways, valves, and flow cell 101 by pumps, gas pressure, or other suitable methods, and may be discarded into the waste container 106 after exiting the outlet 103 of the flow cell 101. The fluidics controller 118 may control driving forces for the reagents 114 and the operation of valve 112 and valve block 116 with suitable software.

The microwell array 107 includes an array of reaction regions as described herein, also referred to herein as microwells, which are operationally associated with corresponding chemical sensors in the sensor array. For example, each reaction region may be coupled to a chemical sensor suitable for detecting an analyte or reaction property of interest within that reaction region. The microwell array 107 may be integrated in the integrated circuit device 100, so that the microwell array 107 and the sensor array are part of a single device or chip.

The flow cell 101 may have a variety of configurations for controlling the path and flow rate of reagents 114 over the microwell array 107. The array controller 124 provides bias voltages and timing and control signals to the integrated circuit device 100 for reading the chemical sensors of the sensor array. The array controller 124 also provides a reference bias voltage to the reference electrode 108 to bias the reagents 114 flowing over the microwell array 107.

During an experiment, the array controller 124 collects and processes output signals from the chemical sensors of the sensor array through output ports on the integrated circuit device 100 via bus 127. The array controller 124 may be a computer or other computing means. The array controller 124 may include memory for storage of data and software applications, a processor for accessing data and executing applications, and components that facilitate communication with the various components of the system in FIG. 1.

The values of the output signals of the chemical sensors indicate physical and/or chemical parameters of one or more reactions taking place in the corresponding reaction regions in the microwell array 107. For example, in an exemplary embodiment, the values of the output signals may be processed using the techniques disclosed in Rearick et al., U.S. patent application Ser. No. 13/339,846, filed Dec. 29, 2011, based on U.S. Prov. Pat. Appl. Nos. 61/428,743, filed Dec. 30, 2010, and 61/429,328, filed Jan. 3, 2011, and in Hubbell, U.S. patent application Ser. No. 13/339,753, filed Dec. 29, 2011, based on U.S. Prov. Pat. Appl. No. 61/428,097, filed Dec. 29, 2010, which are all incorporated by reference herein in their entirety.

The user interface 128 may display information about the flow cell 101 and the output signals received from chemical sensors in sensor array on the integrated circuit device 100. The user interface 128 may also display instrument settings and controls, and allow a user to enter or set instrument settings and controls.

In an exemplary embodiment, during the experiment the fluidics controller 118 may control delivery of the individual reagents 114 to the flow cell 101 and integrated circuit device 100 in a predetermined sequence, for predetermined durations, at predetermined flow rates. The array controller 124 can then collect and analyze the output signals of the chemical sensors due to chemical reactions occurring in response to the delivery of the reagents 114.

During the experiment, the system may also monitor and control the temperature of the integrated circuit device 100, so that reactions take place and measurements are made at a known predetermined temperature.

The system may be configured to let a single fluid or reagent contact the reference electrode 108 throughout an entire multi-step reaction during operation. The valve 112 may be shut to prevent any wash solution 110 from flowing into passage 109 as the reagents 114 are flowing. Although the flow of wash solution may be stopped, there may still be uninterrupted fluid and electrical communication between the reference electrode 108, passage 109, and the microwell array 107. The distance between the reference electrode 108 and the junction between passages 109 and 111 may be selected so that little or no amount of the reagents flowing in passage 109 and possibly diffusing into passage 111 reach the reference electrode 108. In an exemplary embodiment, the wash solution 110 may be selected as being in continuous contact with the reference electrode 108, which may be especially useful for multi-step reactions using frequent wash steps.

Figure 2:
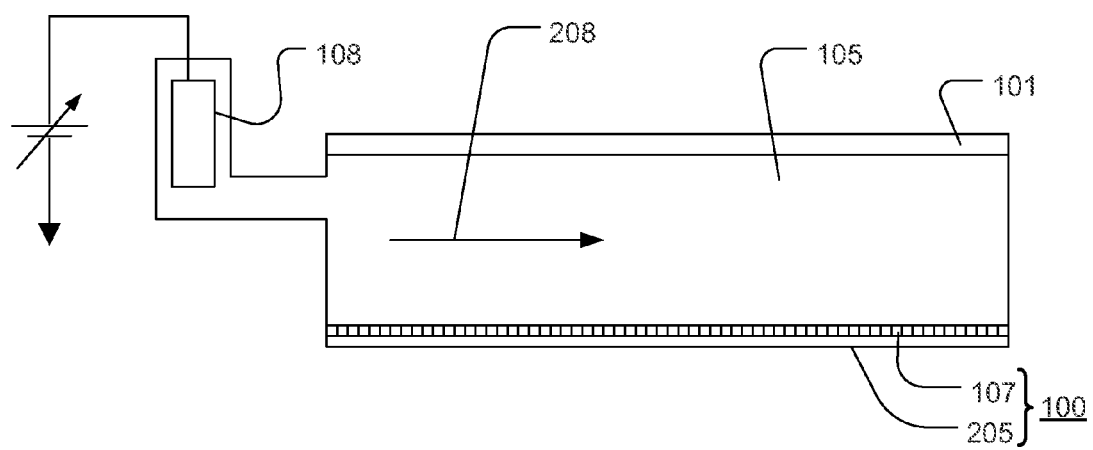
FIG. 2 illustrates a cross-sectional view of a portion of the integrated circuit device and flow cell according to an exemplary embodiment.

FIG. 2 illustrates cross-sectional and expanded views of a portion of the integrated circuit device 100 and flow cell 101. During operation, the flow chamber 105 of the flow cell 101 confines a reagent flow 208 of delivered reagents across open ends of the reaction regions in the microwell array 107. The volume, shape, aspect ratio (such as base width-to-well depth ratio), and other dimensional characteristics of the reaction regions may be selected based on the nature of the reaction taking place, as well as the reagents, byproducts, or labeling techniques (if any) that are employed.

The chemical sensors of the sensor array 205 are responsive to (and generate output signals) chemical reactions within associated reaction regions in the microwell array 107 to detect an analyte or reaction property of interest. The chemical sensors of the sensor array 205 may for example be chemically sensitive field-effect transistors (chemFETs), such as ion-sensitive field effect transistors (ISFETs). Examples of chemical sensors that may be used in embodiments are described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

Figure 3A:
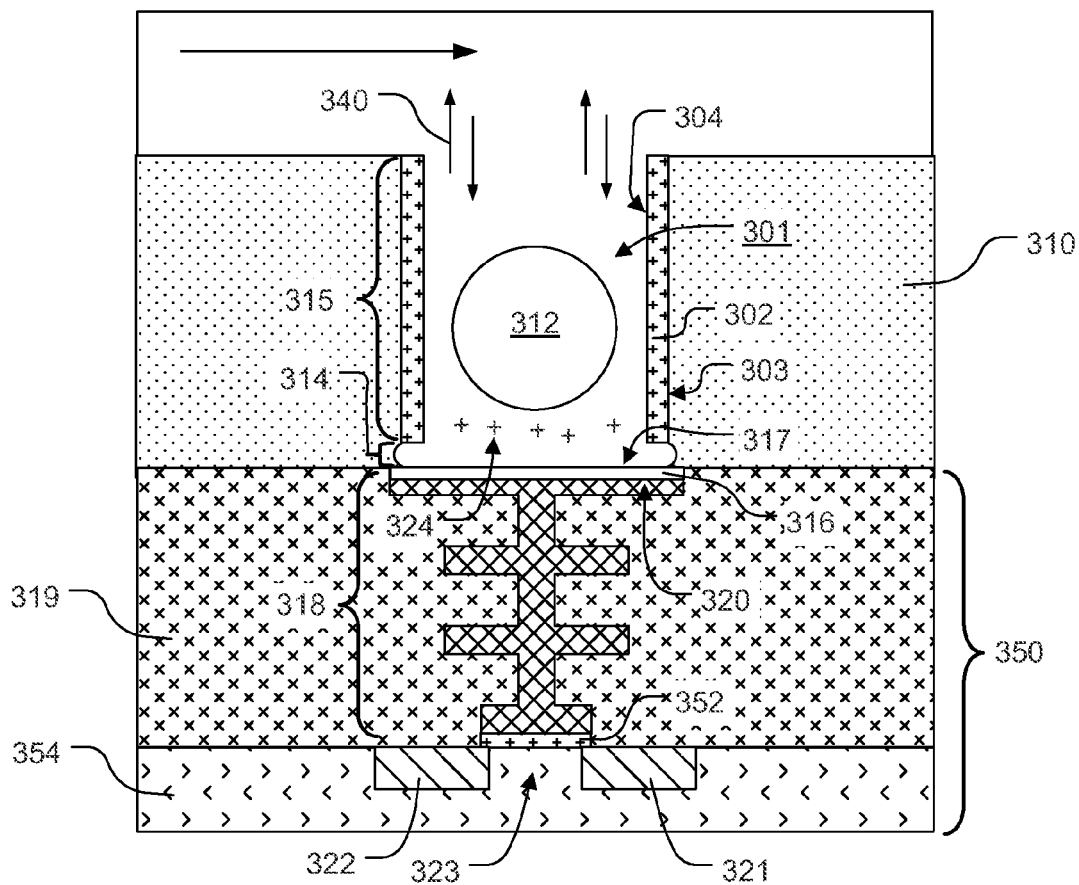
FIGS. 3A and 3B illustrate cross-sectional and top views respectively of a representative chemical sensor and corresponding reaction region according to an exemplary embodiment.
Figure 3B:
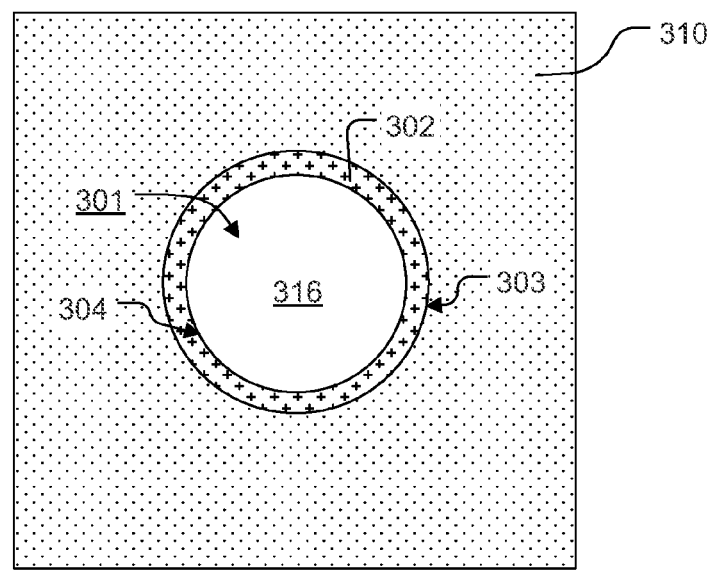

FIGS. 3A and 3B illustrate cross-sectional and top views respectively of a representative chemical sensor 350 in the sensor array coupled to a corresponding reaction region 301 in the microwell array according to an exemplary embodiment.

In the illustrated example, the chemical sensor 350 is an ion-sensitive field effect transistor. The chemical sensor 350 includes a floating gate structure 318 having a sensor plate 320 separated from the reaction region 301 by an ion-sensitive layer 316. In the illustrated example, the floating gate structure 318 includes multiple patterned layers of conductive material within layers of dielectric material 319. As described in more detail below, the upper surface of the ion-sensitive layer 316 acts as the sensing surface 317 for the chemical sensor 350.

The ion-sensitive layer 316 may be deposited using various techniques, or naturally grown during one or more of the manufacturing processes used to form the chemical sensor 350. In some embodiments, the ion-sensitive layer 316 is a metal oxide, such as an oxide of silicon, tantalum, aluminum, lanthanum, titanium, zirconium, hafnium, tungsten, palladium, iridium, etc.

The ion-sensitive layer 316 may for example be an oxide of the upper layer of conductive material of the sensor plate 220. For example, the upper layer of the sensor plate 320 may be titanium nitride, and the ion-sensitive layer 316 may comprise titanium oxide or titanium oxynitride. More generally, the ion-sensitive layer 316 may comprise a variety of different materials to facilitate sensitivity to particular ions. For example, silicon nitride or silicon oxynitride, as well as metal oxides such as silicon oxide, aluminum or tantalum oxides, generally provide sensitivity to hydrogen ions, whereas layers comprising polyvinyl chloride containing valinomycin provide sensitivity to potassium ions. Materials sensitive to other ions such as sodium, silver, iron, bromine, iodine, calcium, and nitrate may also be used.

The chemical sensor 350 also includes a source region 321 and a drain region 322 within a semiconductor substrate 354. The source region 321 and the drain region 322 comprise doped semiconductor material have a conductivity type different from the conductivity type of the substrate 354.

Channel region 323 separates the source region 321 and the drain region 322. The floating gate structure 318 overlies the channel region 323, and is separated from the substrate 354 by a gate dielectric 352. The gate dielectric 352 may be for example silicon dioxide. Alternatively, other dielectrics may be used for the gate dielectric 352.

An opening extends through dielectric material 310 to the ion-sensitive layer 316. The dielectric material 310 may comprise one or more layers of material deposited sequentially. The opening includes a lower portion 314 proximate to the ion-sensitive layer 316. An upper portion 315 of the opening extends from the lower portion 314 to the upper surface of the dielectric material 310.

The upper portion 315 of the opening includes a sidewall spacer 302 on a sidewall 303 of the dielectric material 310. As shown in FIG. 3A, the sidewall spacer 302 does not extend down the entire opening to the ion-sensitive layer 316. Instead, the sidewall spacer 302 has a bottom surface spaced away from the ion-sensitive layer 316 by the lower portion 314 of the opening.

The sidewall spacer 302 includes an inner surface 304 defining an upper segment of the reaction region 301. A lower segment of the reaction region 301 is defined by the lower portion 314 of the opening. As a result of this structure, the sidewall spacer 302 overhangs the lower portion 314 of the opening, such that the width of the lower segment of the reaction region 301 is greater than the width of the upper segment of the reaction region 301.

The opening through the dielectric material 310 is formed using a two step etching process, as described in more detail below with respect to FIGS. 4-8. A first etch process partially etches the dielectric material 310 to define the upper portion 315 of the opening, and leave remaining dielectric material 310 over the ion-sensitive layer 316. The first etch process may be a process which, if continued all the way down to the ion-sensitive layer 316, would cause significant charge to accumulate on the floating gate structure 318. However, by leaving remaining dielectric material 310 on the ion-sensitive layer 316, such charge accumulation is precluded. For example, first etch process may for example be a directional etching process such as RIE, so that the opening can have a high aspect ratio and be accurately and repeatedly defined, while also not contributing to noise in the chemical sensor 350.

The sidewall spacer 302 is then formed on the sidewall 303. The dielectric material 310 at the lower portion 314 of the opening comprises material that can be selectively etched relative to the material of the sidewall spacer 302. For example, in one embodiment, the dielectric material 310 at the lower portion 314 of the opening comprises silicon dioxide, and the sidewall spacer 302 comprises silicon nitride. Alternatively, other dielectric and/or electrically conductive materials may be used. For example, in some embodiments the sidewall spacer 302 may comprise an electrically conductive material such as titanium nitride. An electrically conductive material for the sidewall spacer 302 can reduce the thermal resistance of the reaction region 301 when containing solution, which in turn can reduce the overall thermal noise during operation.

The sidewall spacer 302 then serves as an etch protect layer to retain the shape of the upper portion 315 during a second etch process used to form the lower portion 314. This second etch process continues the opening and exposes the ion-sensitive layer 316 to define the reaction region 301.

The second etching process may for example be a wet etch process which does not contribute charge accumulation on the floating gate structure 318. Applicants have found that a significant amount of the total noise in ISFETs, can be attributed to the use of high-power directional etching processes involved in forming the reaction regions. In particular, using plasma to etch all the way down to the ion-sensitive layer 316 can subject the floating gate structure 318 to the plasma for prolonged periods of time. The plasma can cause charge build up on the floating gate structure 318, to the point of causing undesirable changes or damage to the device. This accumulated charge can become trapped in the gate dielectric 352 and/or the interface between the gate dielectric 352 and the semiconductor substrate 354, thereby contributing to the noise and resulting in variations in operation and degradation in performance.

By using a second etching process to which does not accumulate charge on the floating gate structure 318, noise induced in the chemical sensor 350 due to the formation of the reaction region 301 can be eliminated. As a result, the techniques described herein can be used to form low noise chemical sensors with uniform performance across an array, such that the characteristics of chemical reactions can be accurately measured.

As shown in the top view of FIG. 3B, in the illustrated example the opening and the reaction region 301 have circular cross sections. Alternatively, these may be non-circular. For example, the cross-section may be hexagonal.

In operation, the chemical sensor 350 is responsive to (and generates an output signal related to) the amount of a charge 324 present on ion-sensitive layer 316 opposite the sensor plate 320. Changes in the charge 324 cause changes in the voltage on the floating gate structure 318, which in turn changes in the threshold voltage of the transistor. This change in threshold voltage can be measured by measuring the current in the channel region 323 between the source region 321 and a drain region 322. As a result, the chemical sensor 350 can be used directly to provide a current-based output signal on an array line connected to the source region 321 or drain region 322, or indirectly with additional circuitry to provide a voltage-based output signal. Reactants, wash solutions, and other reagents may move in and out of the reaction region 301 by a diffusion mechanism 340.

In an embodiment, reactions carried out in the reaction region 301 can be analytical reactions to identify or determine characteristics or properties of an analyte of interest. Such reactions can generate directly or indirectly byproducts that affect the amount of charge adjacent to the sensor plate 320. If such byproducts are produced in small amounts or rapidly decay or react with other constituents, multiple copies of the same analyte may be analyzed in the reaction region 301 at the same time in order to increase the output signal generated. In an embodiment, multiple copies of an analyte may be attached to a solid phase support 312, either before or after deposition into the reaction region 301. The solid phase support 312 may be microparticles, nanoparticles, beads, solid or porous comprising gels, or the like. For simplicity and ease of explanation, solid phase support 312 is also referred herein as a particle. For a nucleic acid analyte, multiple, connected copies may be made by rolling circle amplification (RCA), exponential RCA, or like techniques, to produce an amplicon without the need of a solid support.

In various exemplary embodiments, the methods, systems, and computer readable media described herein may advantageously be used to process and/or analyze data and signals obtained from electronic or charged-based nucleic acid sequencing. In electronic or charged-based sequencing (such as, pH-based sequencing), a nucleotide incorporation event may be determined by detecting ions (e.g., hydrogen ions) that are generated as natural by-products of polymerase-catalyzed nucleotide extension reactions. This may be used to sequence a sample or template nucleic acid, which may be a fragment of a nucleic acid sequence of interest, for example, and which may be directly or indirectly attached as a clonal population to a solid support, such as a particle, microparticle, bead, etc. The sample or template nucleic acid may be operably associated to a primer and polymerase and may be subjected to repeated cycles or "flows" of deoxynucleoside triphosphate ("dNTP") addition (which may be referred to herein as "nucleotide flows" from which nucleotide incorporations may result) and washing. The primer may be annealed to the sample or template so that the primer's 3' end can be extended by a polymerase whenever dNTPs complementary to the next base in the template are added. Then, based on the known sequence of nucleotide flows and on measured output signals of the chemical sensors indicative of ion concentration during each nucleotide flow, the identity of the type, sequence and number of nucleotide(s) associated with a sample nucleic acid present in a reaction region coupled to a sensor can be determined.

FIGS. 4 to 8 illustrate stages in a manufacturing process for forming a low noise chemical sensor and corresponding well structure according to an exemplary embodiment.

Figure 4:
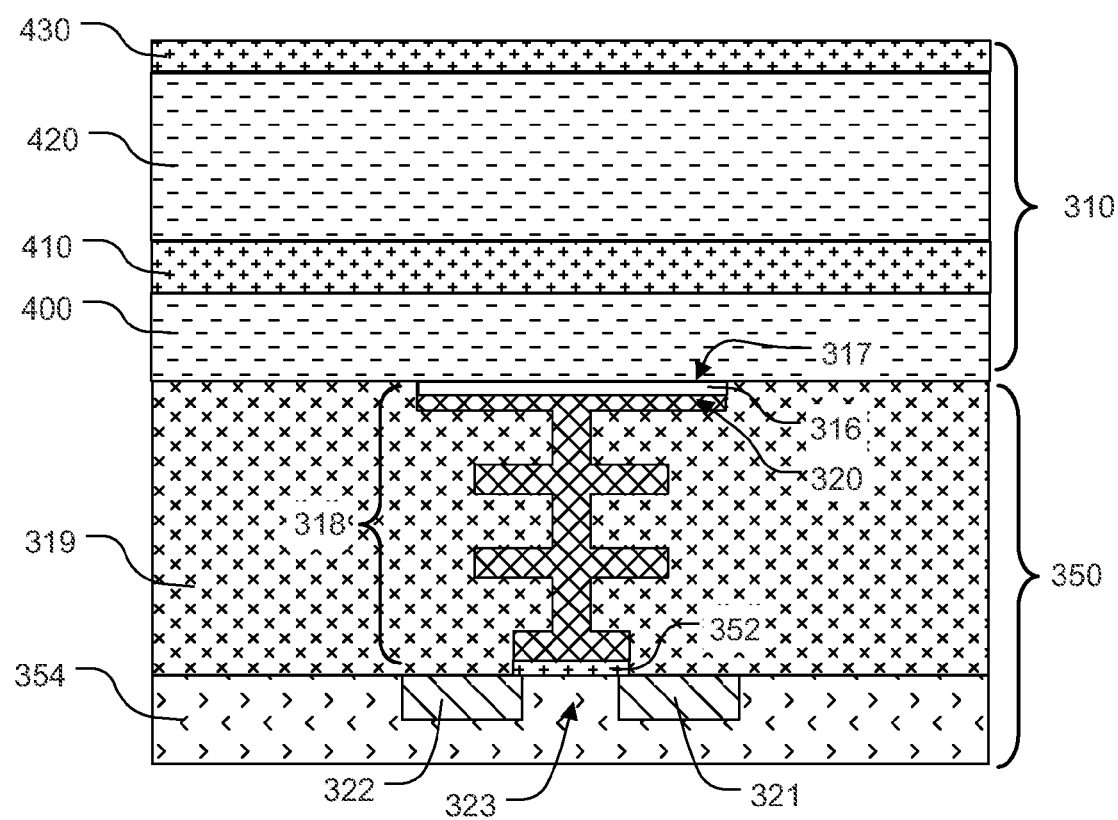
FIGS. 4 to 8 illustrate stages in a manufacturing process for forming a low noise chemical sensor and corresponding well structure according to an exemplary embodiment.

FIG. 4 illustrates a first stage of forming a dielectric material 310 on the sensing surface 317 of a chemical sensor 350. In the illustrated example, the chemical sensor 350 is the ion-sensitive field effect transistor described above and includes ion-sensitive layer 316 having a top surface acting as the sensing surface 317. The chemical sensor 350 may for example be formed using the techniques described in U.S. Patent Application Publication No. 2010/0300559, No. 2010/0197507, No. 2010/0301398, No. 2010/0300895, No. 2010/0137143, and No. 2009/0026082, and U.S. Pat. No. 7,575,865, each which are incorporated by reference herein.

In the illustrated embodiment, the dielectric material 310 is formed by sequentially depositing a first layer 400 of silicon dioxide, a second layer 410 of silicon nitride, a third layer 420 of silicon dioxide, and a fourth layer 430 of silicon nitride. More generally, the dielectric material 310 may comprise one or more layers, and may comprise various materials.

Figure 5:
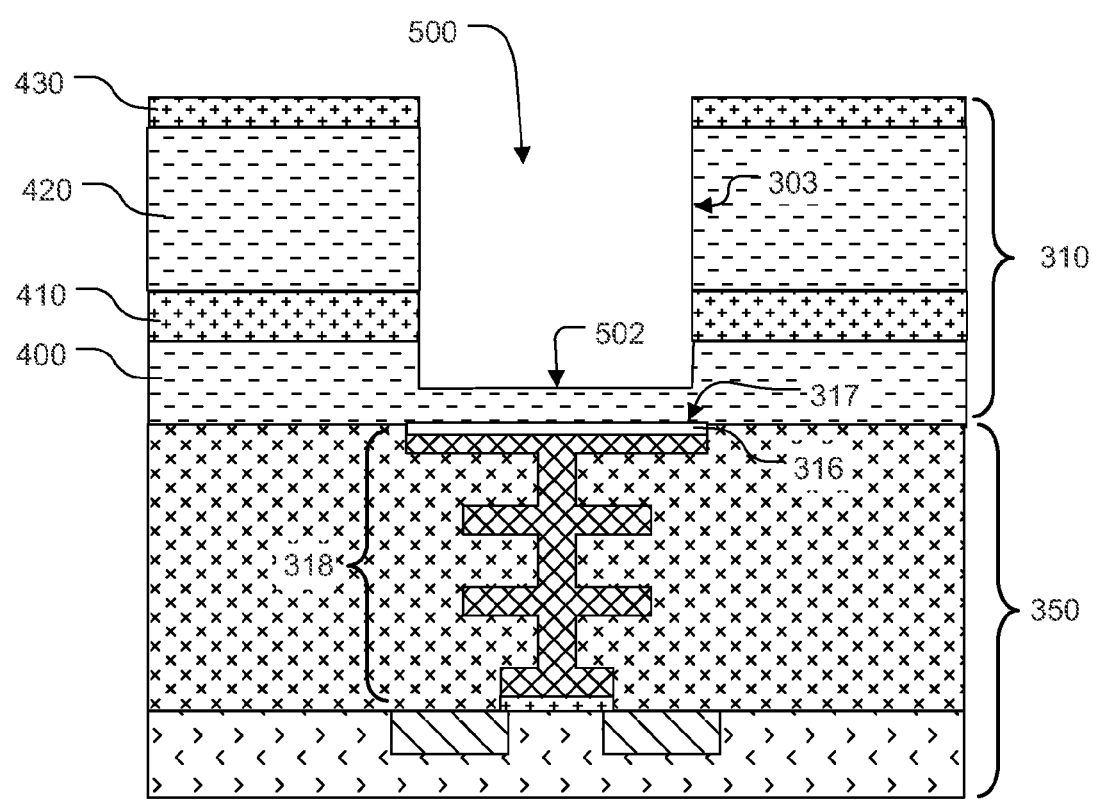

Next, the dielectric material 310 of the structure in FIG. 4 is partially etched using an etch process to define an opening 500 over the sensing surface 317, resulting in the structure illustrated in FIG. 5. As shown in FIG. 5, the opening 500 includes a sidewall 303, and a bottom surface 502 spaced away from the sensing surface 317 by remaining dielectric material 310. This remaining dielectric material 310 prevents the sensing surface 317 from being subjected to this etch process, so that charge does not accumulate. As a result, the etch process used to form the opening 500 may be a directional etch process, such as a plasma etch, so that the opening 500 can be well defined, while at the same time precluding this etching process from increasing the noise in the chemical sensor 350.

The opening 500 may for example be formed by using a lithographic process to pattern a layer of photoresist on the dielectric material 310 to define the location of the opening 500, and then anisotropically etching the dielectric material 310 using the patterned photoresist as an etch mask. The anisotropic etching of the dielectric material 310 may for example be a dry etch process, such as a fluorine based Reactive Ion Etching (RIE) process.

In the illustrated example, the etching of the dielectric material 310 is carried out using RIE with end point detection, so that the etching can stop at or in the first layer 400. The etching may for example be performed using a single etch chemistry to each all the layers 400, 410, 420 and 430. Alternatively, different etch chemistries may be used for each of the layers.

Figure 6:
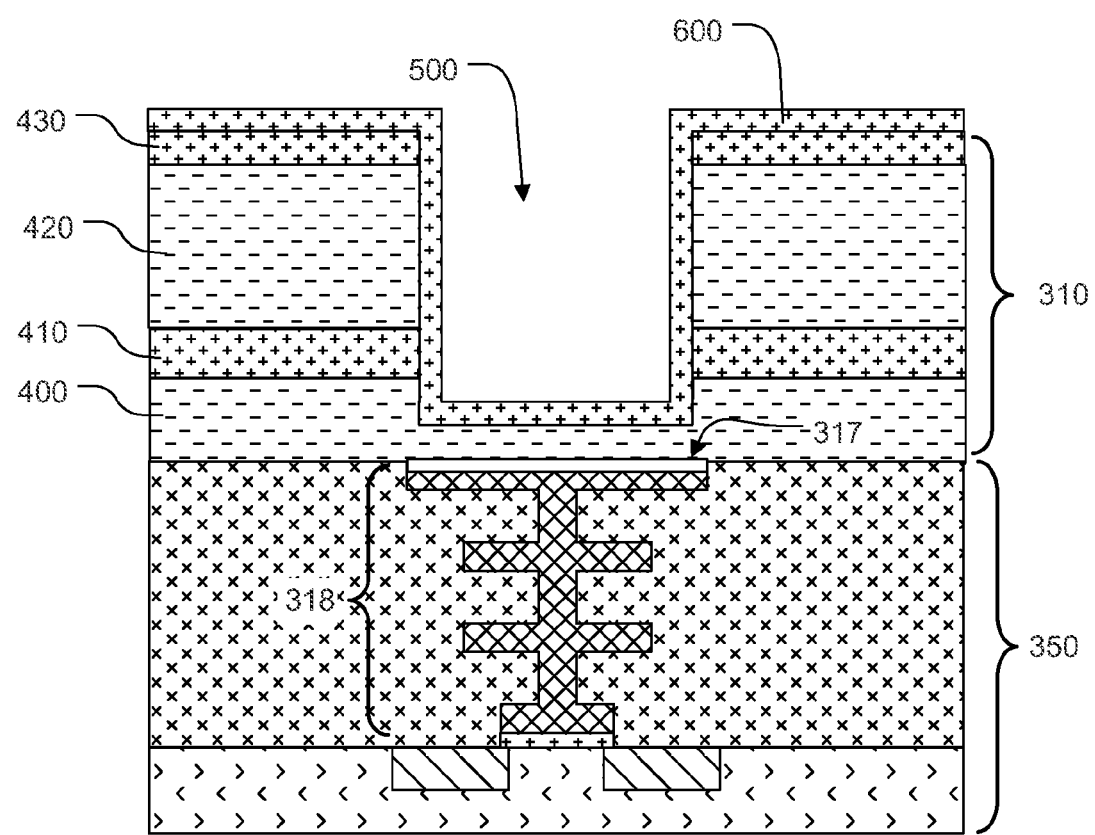

Next, a conformal layer 600 of etch protect material is formed on the structure illustrated in FIG. 5, resulting in the structure illustrated in FIG. 6. In the illustrate embodiment, the conformal layer 600 comprises silicon nitride and is formed using plasma enhanced chemical vapor deposition (PECVD). Alternatively, other procedures and materials may be used. For example, the conformal layer 600 could be deposited by sputtering, atomic layer deposition (ALD), low pressure chemical vapor deposition (LPCVD), etc. As described in more detail below with respect to FIG. 8, the remaining dielectric material 310 over the sensing surface 317 (material of layer 400 in this example) comprises material which can be selectively etched relative to the material of the conformal layer 600 when subjected to a chosen etch process.

Figure 7:
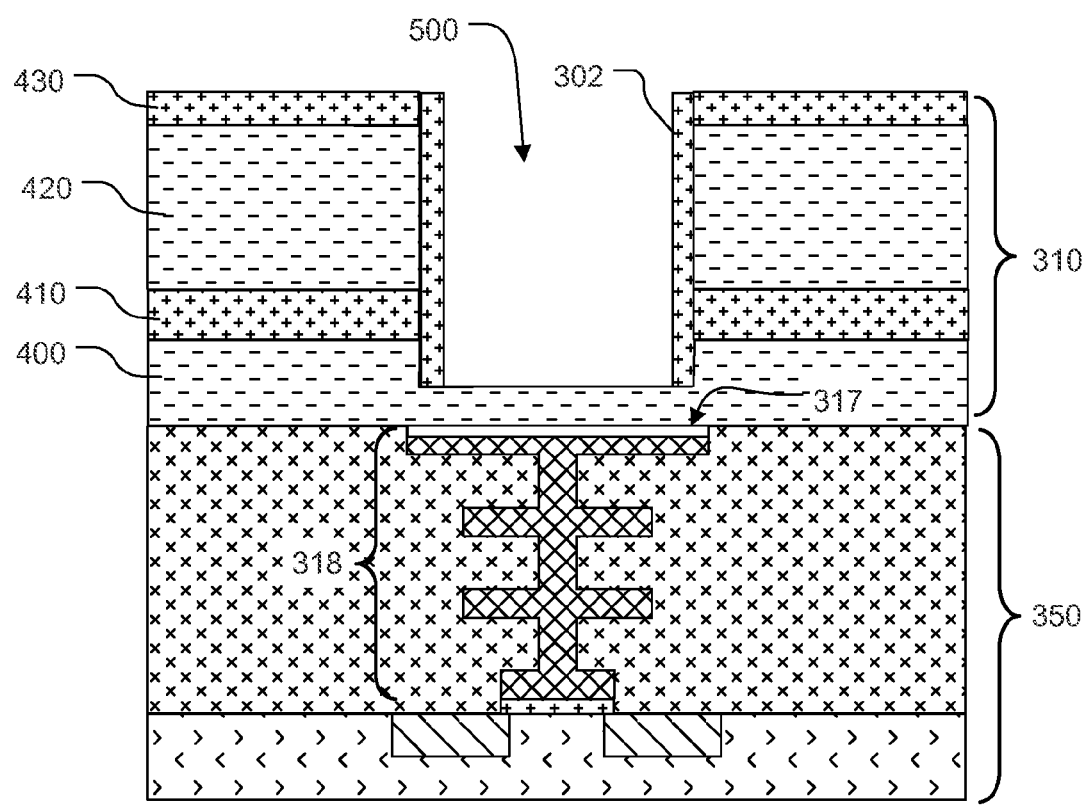

Next, an anisotropic etching process is performed on the conformal layer 600 illustrated in FIG. 6 to form a sidewall spacer 302 of remaining material of layer 600 within the opening, resulting in the structure illustrated in FIG. 7. The anisotropic etching process removes the material of the conformal layer 600 on horizontal surfaces at a faster rate than material on vertical surfaces. The anisotropic etching process may for example be performed using a RIE or other plasma etching process. Alternatively, other etching processes may be used.

Figure 8:
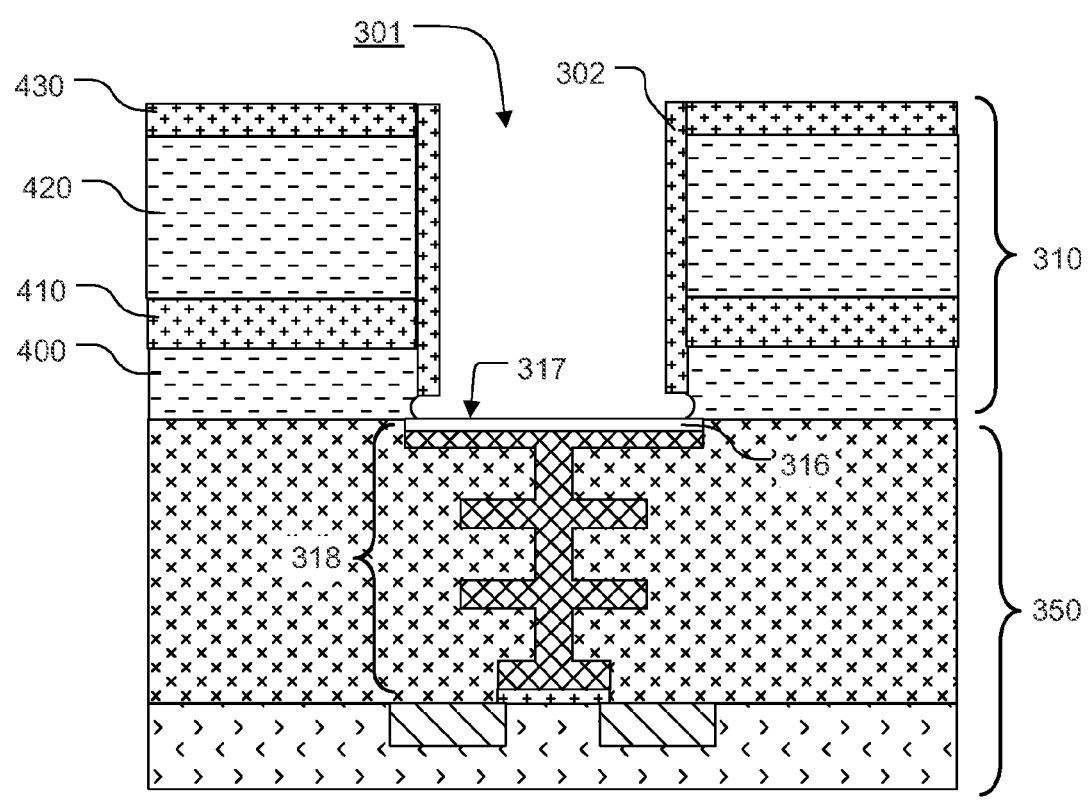

Next, an isotropic etching process is performed on the structure illustrated in FIG. 7 to extend the opening 500 down to the sensing surface 317 using the sidewall spacer 302 as an etch mask, thereby forming the reaction region 301 and resulting in the structure illustrated in FIG. 8. The isotropic etching process selectively etches material of the layer 400, relative to the material of the sidewall spacer 302. As a result, the sidewall spacer 302 acts to protect and retain the shape of the upper portion of the opening.

The isotropic etching process may for example be a wet etch process, such as a buffered oxide etch, HF etch chemistry, etc. Alternatively, other etch processes and chemistries may be used.

A wet process results in no charge accumulation on the floating gate structure 318. As a result, noise induced in the chemical sensor 350 can be significantly reduced, as compared to the use of directional etch processes (e.g. plasma etching) to etch down to the sensing surface 317. In doing so, the techniques described herein can be used to form low noise chemical sensors with uniform performance across an array, such that the characteristics of subsequent chemical reactions can be accurately measured.

While the present invention is disclosed by reference to the preferred embodiments and examples detailed above, it is to be understood that these examples are intended in an illustrative rather than in a limiting sense. It is contemplated that modifications and combinations will readily occur to those skilled in the art, which modifications and combinations will be within the spirit of the invention and the scope of the following claims.

What is claimed is:

1. A chemical detection device, comprising:
   a plurality of chemical sensors each having respective sensing surfaces;
   a dielectric material having openings extending to the sensing surfaces, the openings having sidewalls, the dielectric material having a top surface extending between adjacent openings; and
   a plurality of sidewall spacers on the sidewalls of the openings and not on the top surface of the dielectric material, the sidewall spacers having a bottom most surface spaced away from the sensing surfaces such that the sidewall spacer does not contact the surfaces, the sidewall spacers each having an inside surface defining a reaction region for receiving at least one reactant.

2. The chemical detection device of claim 1, wherein the dielectric material within a lower portion of the openings comprises material different than that of the plurality of sidewall spacers.

3. The chemical detection device of claim 1, wherein the chemical sensors are chemically-sensitive field effect transistors, and the sensing surfaces are coupled to respective channels of the chemically-sensitive field effect transistors.

4. The chemical detection device of claim 3, wherein the sensing surfaces are on an upper surface of respective floating gates of the chemically-sensitive field effect transistors.

5. The chemical detection device of claim 1, wherein the chemical sensors generate respective sensor signals in response to a chemical reaction occurring within a given reaction region.

6. The chemical detection device of claim 5, wherein the chemical reaction is a sequencing reaction.

* * * * *